(12) United States Patent
Last

(10) Patent No.: US 10,174,275 B2
(45) Date of Patent: Jan. 8, 2019

(54) THERMALLY OPENING STABLE CORE/SHELL MICROCAPSULES

(71) Applicant: FOLLMANN GMBH & CO. KG, Minden (DE)

(72) Inventor: Klaus Last, Minden (DE)

(73) Assignee: FOLLMANN GMBH & CO. KG, Minden (DE)

( * ) Notice: Subject to any disclaimer, the term of this patent is extended or adjusted under 35 U.S.C. 154(b) by 283 days.

(21) Appl. No.: 14/609,451

(22) Filed: Jan. 30, 2015

(65) Prior Publication Data

US 2016/0222328 A1    Aug. 4, 2016

(51) Int. Cl.

| | | |
|---|---|---|
| C11D 17/00 | (2006.01) |
| C11D 3/50 | (2006.01) |
| C08G 14/10 | (2006.01) |
| C08J 9/22 | (2006.01) |
| A61K 8/11 | (2006.01) |
| C08J 9/32 | (2006.01) |
| C11D 1/62 | (2006.01) |
| C11D 3/20 | (2006.01) |
| C11D 3/37 | (2006.01) |
| B01J 13/14 | (2006.01) |
| B01J 13/20 | (2006.01) |
| C09B 67/02 | (2006.01) |
| A61K 8/36 | (2006.01) |
| A61K 8/40 | (2006.01) |
| A61K 8/41 | (2006.01) |
| A61K 8/42 | (2006.01) |
| A61K 8/49 | (2006.01) |
| A61Q 19/00 | (2006.01) |
| A61K 8/81 | (2006.01) |
| A61K 8/84 | (2006.01) |
| A61K 8/19 | (2006.01) |
| A61Q 13/00 | (2006.01) |

(52) U.S. Cl.
CPC ............ *C11D 3/505* (2013.01); *A61K 8/11* (2013.01); *A61K 8/19* (2013.01); *A61K 8/361* (2013.01); *A61K 8/40* (2013.01); *A61K 8/416* (2013.01); *A61K 8/42* (2013.01); *A61K 8/494* (2013.01); *A61K 8/817* (2013.01); *A61K 8/8152* (2013.01); *A61K 8/8176* (2013.01); *A61K 8/84* (2013.01); *A61Q 19/00* (2013.01); *B01J 13/14* (2013.01); *B01J 13/206* (2013.01); *C08G 14/10* (2013.01); *C08J 9/32* (2013.01); *C09B 67/0097* (2013.01); *C11D 1/62* (2013.01); *C11D 3/2079* (2013.01); *C11D 3/3719* (2013.01); *C11D 3/3776* (2013.01); *C11D 17/0039* (2013.01); *A61K 2800/10* (2013.01); *A61K 2800/22* (2013.01); *A61K 2800/412* (2013.01); *A61Q 13/00* (2013.01); *C10N 2250/16* (2013.01)

(58) Field of Classification Search
None
See application file for complete search history.

(56) References Cited

U.S. PATENT DOCUMENTS

| | | |
|---|---|---|
| 4,406,816 A | 9/1983 | Sliwka |
| 4,898,696 A | 2/1990 | Sliwka |
| 5,162,486 A | 11/1992 | Follmann et al. |
| 5,260,069 A | 11/1993 | Chen |
| 6,143,276 A | 11/2000 | Unger |
| 6,165,667 A | 12/2000 | Takagi et al. |
| 2003/0004226 A1 | 1/2003 | Hoffman et al. |
| 2003/0049698 A1* | 3/2003 | Wang ............... G01N 33/74 435/7.21 |
| 2004/0018327 A1* | 1/2004 | Wynn ............... A23G 1/54 428/35.7 |
| 2006/0052512 A1 | 3/2006 | Yamauchi |
| 2010/0190674 A1* | 7/2010 | Smets ............... A61K 8/11 510/107 |
| 2011/0171349 A1 | 7/2011 | Poortinga et al. |
| 2012/0122694 A1 | 5/2012 | Last et al. |
| 2012/0128747 A1 | 5/2012 | Véronique et al. |
| 2013/0137626 A1 | 5/2013 | Last et al. |

FOREIGN PATENT DOCUMENTS

| | | |
|---|---|---|
| EP | 0 026 914 A1 | 4/1981 |
| EP | 0 218 887 A2 | 4/1987 |
| EP | 0 415 273 A2 | 3/1991 |
| EP | 2 732 803 A1 | 5/2014 |
| JP | 2005-115194 A | 4/2005 |
| KR | 1020050084965 A | 8/2005 |
| WO | WO 01/51197 A | 7/2001 |
| WO | WO 2009/015872 A1 | 2/2009 |
| WO | WO 2010/014011 A1 | 2/2010 |
| WO | WO 2010/102830 A2 | 9/2010 |
| WO | WO 2011/110368 A2 | 9/2011 |
| WO | WO2013/032447 A1 * | 3/2013 |

OTHER PUBLICATIONS

W. Wang et al.: "Microfluidic Preparation of Multicompartment Microcapsules for Co-Encapsulation and Controlled Release of Multiple Components", Minneapolis Convention Center, Poster Abstract, p. 1 (Oct. 19, 2011).

\* cited by examiner

*Primary Examiner* — Lorna M Douyon
(74) *Attorney, Agent, or Firm* — Norman B. Thot

(57) ABSTRACT

The present invention provides a microcapsule comprising a shell and a core. The core comprises at least one active ingredient and at least one surface-modified disintegrant.

15 Claims, 6 Drawing Sheets a)

b)

a)

b)

THERMALLY OPENING STABLE CORE/SHELL MICROCAPSULES

CROSS REFERENCE TO PRIOR APPLICATIONS

The present invention was previously published as European Patent Application No. 12007807.6, filed Nov. 19, 2012. The entire disclosure of said application is incorporated by reference herein.

FIELD

The present invention relates to thermally opening microcapsules. The present invention relates in particular to microcapsules having surface-modified disintegrants. In addition, the present invention relates to a method for producing the surface-modified disintegrants and the microcapsules containing them. Microcapsules which can contain as core material solid, liquid or gaseous substances are known in the prior art and in recent years have been used in a multiplicity of applications. In this case, it is necessary in particular to give emphasis to their property of enclosing an active ingredient for some time and then releasing it. This is of particular interest, e.g., in the detergent and cleaning agent industry, in which means are produced in order to provide textiles with a long-lasting fragrance. A microencapsulation of the fragrance materials ensures that they are released over a certain period.

BACKGROUND

The very highly controlled release of the contents (core materials) of capsules is also of the greatest interest in other sectors such as, e.g., in the case of self-repairing materials, in food preservation, or in the release of pharmaceuticals or catalysts. To date, various methods for encapsulating active ingredients and the release thereof have been developed. From the pharmaceutical sector, it has long been known that capsules, after intake by the patient, are broken down in the digestive tract and thus release the active ingredients. These capsules can contain disintegrants which take up liquid in the digestive tract, and as a result swell greatly, and mechanically destroy the capsule sheath.

In addition, chemical types of release, for instance in the field of corrosion protection, are known.

External influences lead to a decomposition via, for example, a depolymerisation of the capsule sheath, and thereby to a release of the contents of the capsules. Also, photo-induced openings of capsules are described in the prior art. This includes the targeted destruction of the capsule sheath, for instance using a laser, initiating the depolymerisation of the capsule sheath, or vaporizing the contents, which leads to a disintegration of the capsule sheath. Also, electrical stimulations for the opening of capsule walls are known in the field of self-repairing electronic components and circuits. This necessitates, however, the incorporation of highly functional groups or monomers into the polymeric capsule sheath. This necessity also exists in the field of the magnetic opening of microcapsules by the incorporation of magnetically excitable functionalities, molecules, or particles on a nanocomponent size. Thermal openings are also known, e.g., via initiating the shrinkage of the capsule sheath, by thermal destruction, or by disintegrating the sheath via a pressure increase which is initiated by vaporizing the liquid core contents. Such a thermally triggered release of contents is used, for example, in the release of fragrances or deodorizing substances in cosmetics.

A disadvantage in all these opening mechanisms, however, is that they always require close matching of capsule characteristics such as wall thickness, crosslinking density, permeability, chemical composition, mechanical properties, capsule size, capsule surroundings and capsule contents. In addition, these capsule systems do not correspond to the stable core/shell systems used in industry which protect their core materials from escaping over long periods owing to their particular tightness and chemical resistance. In the case of opening mechanisms such as chemical or electrical opening, opening by light stimuli and by chemical stimuli, use is made, i.e., of the change of conformations in azo dyes, the cleavage of disulphide bonds or acetates, depolymerisation of the capsule wall by cleavage of carbamates or lipid bridges by enzymes or pH changes. This necessitates, however, the incorporation of functions into the wall material which is thereby adversely affected, for example, with respect to its crosslinking density. A high functional density is additionally required for rapid opening. The situation is similar in thermomechanical opening via electrical or magnetic stimuli. The incorporation of metal-containing nanoparticles into the capsule wall is here known which are excited to perform oscillations by applying a magnetic field or electric field, as a result of which heat is generated and thus the capsule wall destroyed. A disadvantage here is the high energy input necessitated thereby, and also the necessity of expensive special apparatuses and equipment with which the opening of the capsules and thus the release of the contents can be effected.

The simplest methods for opening microcapsules are the purely mechanically based systems, for example, crushing or squeezing the capsules.

Opening the microcapsules by thermal stimuli is of particular interest since it is easier to control and meter and can also be employed with microcapsules which are in solution or in dispersion or are in or on living creatures.

Particles have previously been described which undergo an expansion when thermal stimuli are applied. KR-A-2005/0084965, for example, describes a thermally expandable particle comprising a polymeric sheath and a volatile content which converts to the gas phase at a temperature below the softening point of the polymer. Targeted release of contents at a defined temperature is not taught, but only the thermal induced expansion of a microcapsule.

WO-A-2010/014011 describes a particle which has a polymeric sheath and contains a disintegrant which swells with water, which disintegrant, at physiological temperatures and pHs, takes up water and, after the patient takes in the particle, the capsule opens in the digestive tract of the patient and the contents thereof can thereby be released.

W. Wang et al. (Microfluidic Preparation of Multicompartment Microcapsules for Co-Encapsulation and Controlled Release of Multiple Components, Poster abstract, 19 Oct. 2011, Minneapolis Convention Center) describes a particle having a plurality of encapsulated oil kernels and a sheath which contracts on temperature elevation, tearing and thus releasing the oil kernels. A modification of the sheath for a shrinkage on change of the pH or on supply of other external stimuli such as, for example, glucose, is also described.

To date, no microcapsule has yet been described which, within a narrow temperature range, reproducibly opens with high discharge of the contents thereof and simultaneously meets the high requirements of an industrially usable system. The requirements of such a system are, i.e., low costs, flexibility with respect to adaptation to clients wishes, applications, and materials to be employed, a scale-up capacity, a favorable cost-benefit ratio and therefore high economic efficiency, meeting stability guarantees, and general simplicity of the system.

SUMMARY

An aspect of the present invention was to provide an improved thermally opening microcapsule which achieves an improvement compared to the prior art in at least one of these criteria. For example, the capsule wall should open within a narrow temperature range and release the capsule contents rapidly within a narrow time period.

In an embodiment, the present invention provides a microcapsule comprising a shell and a core. The core comprises at least one active ingredient and at least one surface-modified disintegrant.

BRIEF DESCRIPTION OF THE DRAWINGS

The present invention is described in greater detail below on the basis of embodiments and of the drawings in which:

FIG. 1 shows micrographs of a dispersion of the microcapsules in a transparent colorless oil at 25° C. The spherical dark microcapsules may be clearly seen still undamaged against the light background;

FIG. 2 shows micrographs of a dispersion of the microcapsules in a transparent colorless oil at 75° C. The majority of the microcapsules are shown to be still undamaged. The start of opening of some microcapsules may readily be seen on the basis of the light circular regions in the dispersion;

FIG. 3 shows micrographs of a dispersion of the microcapsules in a transparent colorless oil at 85° C. The opening of a multiplicity of the microcapsules is seen more clearly than in FIG. 2 at 75° C.;

FIG. 5 a) shows a side view of the device, while FIG. 5 b) shows a plan view of the device; In FIG. 6 a), the encapsulated core material contains a siloxane. In FIG. 6 b), the encapsulated core material does not contain a hydrophobizing agent.

DETAILED DESCRIPTION

Figure 1:
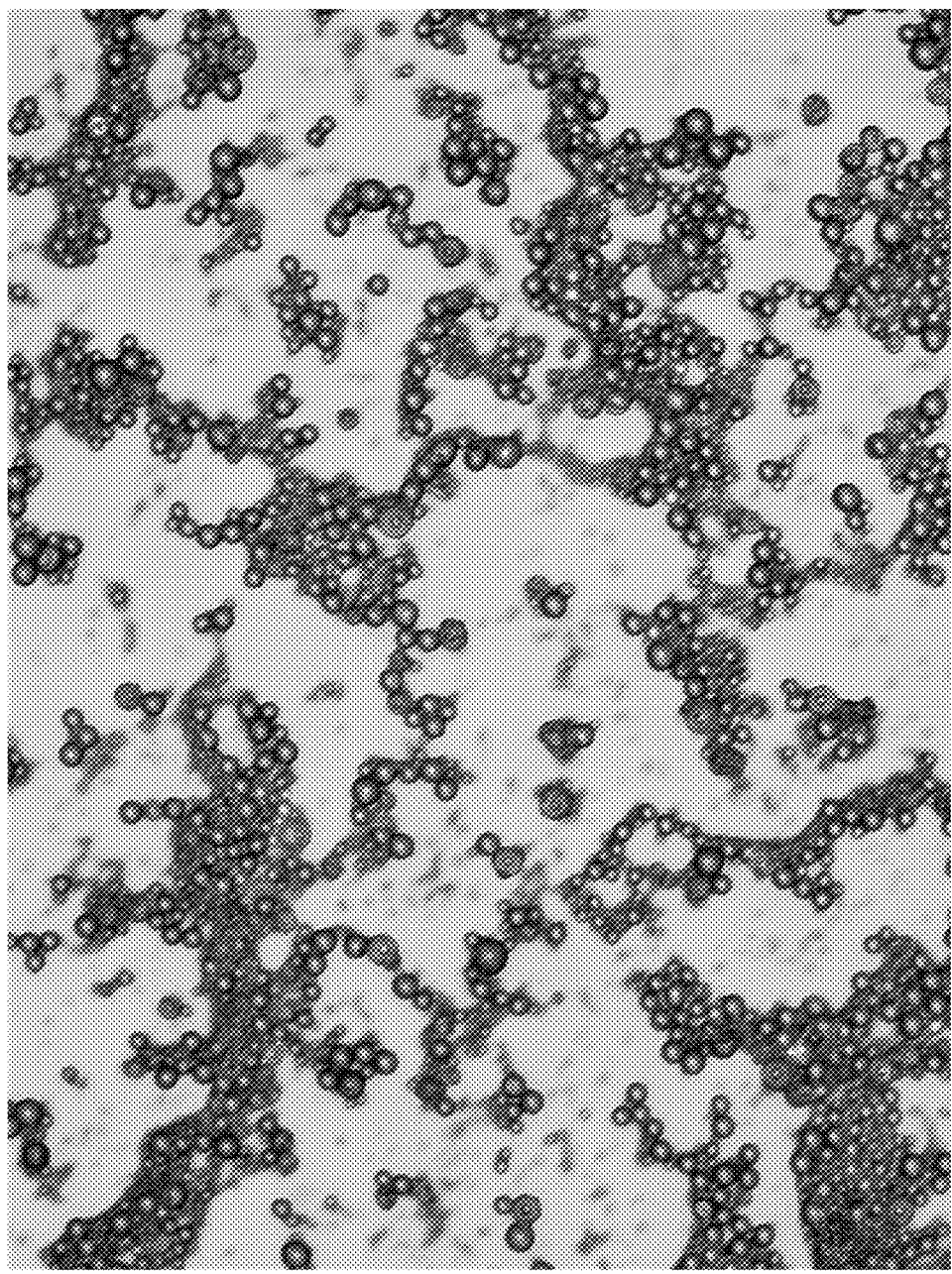
FIG. 1 shows the thermal opening of microcapsules according to the present invention having a melamine-formaldehyde shell.

As material for the capsule walls of the present invention, in particular materials known to a person skilled in the art such as, for example, phenoplast polymers, melamine-formaldehyde polymers, melamine-urea-formaldehyde, polyurethane, gelatine, polyamides, polyacrylates or polyureas are used. These capsule systems exhibit high chemical and physical resistance and form the most stable and tight microcapsules.

Examples of capsule walls for the capsules according to the present invention are known to those skilled in the art, for example, from WO-A-2011/110368, and comprise or consist of an amine, an aldehyde and optionally a (meth) acrylate-AMPS or -AMPP copolymer. AMPS is here taken to mean the 2-acrylamido-2-methylpropanesulphonic acid or salts thereof, and AMPP is taken to mean the 2-acrylamido-2-methylpropanephosphonic acid or salts thereof. Examples of capsule walls of such compounds include:

phloroglucinol, glutardialdehyde, AMPS/hydroxyethyl methacrylate copolymer;

phloroglucinol, succindialdehyde, AMPS/hydroxyethyl methacrylate copolymer;

phloroglucinol, glyoxal, AMPS/hydroxyethyl methacrylate copolymer;

phloroglucinol, glyoxylic acid, AMPS/hydroxyethyl methacrylate copolymer;

phloroglucinol, glutardialdehyde, AMPS/hydroxyethyl acrylate copolymer;

phloroglucinol, succindialdehyde, AMPS/hydroxyethyl acrylate copolymer;

phloroglucinol, glyoxal, AMPS/hydroxyethyl acrylate copolymer;

phloroglucinol, glyoxylic acid, AMPS/hydroxyethyl acrylate copolymer;

phloroglucinol, glutardialdehyde, AMPS/hydroxypropyl methacrylate copolymer;

phloroglucinol, succindialdehyde, AMPS/hydroxypropyl methacrylate copolymer;

phloroglucinol, glyoxal, AMPS/hydroxypropyl methacrylate copolymer;

phloroglucinol, glyoxylic acid, AMPS/hydroxypropyl methacrylate copolymer;

phloroglucinol, glutardialdehyde, AMPS/hydroxypropyl acrylate copolymer;

phloroglucinol, succindialdehyde, AMPS/hydroxypropyl acrylate copolymer;

phloroglucinol, glyoxal, AMPS/hydroxypropyl acrylate copolymer;

phloroglucinol, glyoxylic acid, AMPS/hydroxypropyl acrylate copolymer;

phloroglucinol, glutardialdehyde, AMPS/hydroxybutyl methacrylate copolymer;

phloroglucinol, succindialdehyde, AMPS/hydroxybutyl methacrylate copolymer;

phloroglucinol, glyoxal, AMPS/hydroxybutyl methacrylate copolymer;

phloroglucinol, glyoxylic acid, AMPS/hydroxybutyl methacrylate copolymer;

phloroglucinol, glutardialdehyde, AMPS/hydroxybutyl acrylate copolymer;

phloroglucinol, succindialdehyde, AMPS/hydroxybutyl acrylate copolymer;

phloroglucinol, glyoxal, AMPS/hydroxybutyl acrylate copolymer;

phloroglucinol, glyoxylic acid, AMPS/hydroxybutyl acrylate copolymer;

phloroglucinol, glutardialdehyde, AMPS/polyethylene glycol monomethacrylate copolymer;

phloroglucinol succindialdehyde, AMPS/polyethylene glycol monomethacrylate copolymer;

phloroglucinol, glyoxal, AMPS/polyethylene glycol monomethacrylate copolymer;

phloroglucinol, glyoxylic acid, AMPS/polyethylene glycol monomethacrylate copolymer;

phloroglucinol, glutardialdehyde, AMPS/polyethylene glycol monoacrylate copolymer;

phloroglucinol, succindialdehyde, AMPS/polyethylene glycol monoacrylate copolymer;
phloroglucinol, glyoxal, AMPS/polyethylene glycol monoacrylate copolymer;
phloroglucinol, glyoxylic acid, AMPS/polyethylene glycol monoacrylate copolymer;
phloroglucinol, glutardialdehyde, AMPS/polypropylene glycol monomethacrylate copolymer;
phloroglucinol, succindialdehyde, AMPS/polypropylene glycol monomethacrylate copolymer;
phloroglucinol, glyoxal, AMPS/polypropylene glycol monomethacrylate copolymer;
phloroglucinol, glyoxylic acid, AMPS/polypropylene glycol monomethacrylate copolymer;
phloroglucinol, glutardialdehyde, AMPS/polypropylene glycol monoacrylate copolymer;
phloroglucinol, succindialdehyde, AMPS/polypropylene glycol monoacrylate copolymer;
phloroglucinol, glyoxal, AMPS/polypropylene glycol monoacrylate copolymer;
phloroglucinol, glyoxylic acid, AMPS/polypropylene glycol monoacrylate copolymer;
phloroglucinol, glutardialdehyde, AMPS/methoxypolyethylene glycol monomethacrylate copolymer;
phloroglucinol, succindialdehyde, AMPS/methoxypolyethylene glycol monomethacrylate copolymer;
phloroglucinol, glyoxal, AMPS/methoxypolyethylene glycol monomethacrylate copolymer;
phloroglucinol, glyoxylic acid, AMPS/methoxypolyethylene glycol monomethacrylate copolymer;
phloroglucinol, glutardialdehyde, AMPS/methoxypolyethylene glycol monoacrylate copolymer;
phloroglucinol, succindialdehyde, AMPS/methoxypolyethylene glycol monoacrylate copolymer;
phloroglucinol, glyoxal, AMPS/methoxypolyethylene glycol monoacrylate copolymer;
phloroglucinol, glyoxylic acid, AMPS/methoxypolyethylene glycol monoacrylate copolymer;
resorcinol, glutardialdehyde, AMPS/hydroxyethyl methacrylate copolymer;
resorcinol, succindialdehyde, AMPS/hydroxyethyl methacrylate copolymer;
resorcinol, glyoxal, AMPS/hydroxyethyl methacrylate copolymer;
resorcinol, glyoxylic acid, AMPS/hydroxyethyl methacrylate copolymer;
resorcinol, glutardialdehyde, AMPS/hydroxyethyl acrylate copolymer;
resorcinol, succindialdehyde, AMPS/hydroxyethyl acrylate copolymer;
resorcinol, glyoxal, AMPS/hydroxyethyl acrylate copolymer;
resorcinol, glyoxylic acid, AMPS/hydroxyethyl acrylate copolymer;
resorcinol, glutardialdehyde, AMPS/hydroxypropyl methacrylate copolymer;
resorcinol, succindialdehyde, AMPS/hydroxypropyl methacrylate copolymer;
resorcinol, glyoxal, AMPS/hydroxypropyl methacrylate copolymer;
resorcinol, glyoxylic acid, AMPS/hydroxypropyl methacrylate copolymer;
resorcinol, glutardialdehyde, AMPS/hydroxypropyl acrylate copolymer;
resorcinol, succindialdehyde, AMPS/hydroxypropyl acrylate copolymer;
resorcinol, glyoxal, AMPS/hydroxypropyl acrylate copolymer;
resorcinol, glyoxylic acid, AMPS/hydroxypropyl acrylate copolymer;
resorcinol, glutardialdehyde, AMPS/hydroxybutyl methacrylate copolymer;
resorcinol, succindialdehyde, AMPS/hydroxybutyl methacrylate copolymer;
resorcinol, glyoxal, AMPS/hydroxybutyl methacrylate copolymer;
resorcinol, glyoxylic acid, AMPS/hydroxybutyl methacrylate copolymer;
resorcinol, glutardialdehyde, AMPS/hydroxybutyl acrylate copolymer;
resorcinol, succindialdehyde, AMPS/hydroxybutyl acrylate copolymer;
resorcinol, glyoxal, AMPS/hydroxybutyl acrylate copolymer;
resorcinol, glyoxylic acid, AMPS/hydroxybutyl acrylate copolymer;
resorcinol, glutardialdehyde, AMPS/polyethylene glycol monomethacrylate copolymer;
resorcinol, succindialdehyde, AMPS/polyethylene glycol monomethacrylate copolymer;
resorcinol, glyoxal, AMPS/polyethylene glycol monomethacrylate copolymer;
resorcinol, glyoxylic acid, AMPS/polyethylene glycol monomethacrylate copolymer;
resorcinol, glutardialdehyde, AMPS/polyethylene glycol monoacrylate copolymer;
resorcinol, succindialdehyde, AMPS/polyethylene glycol monoacrylate copolymer;
resorcinol, glyoxal, AMPS/polyethylene glycol monoacrylate copolymer;
resorcinol, glyoxylic acid, AMPS/polyethylene glycol monoacrylate copolymer;
resorcinol, glutardialdehyde, AMPS/polypropylene glycol monomethacrylate copolymer;
resorcinol, succindialdehyde, AMPS/polypropylene glycol monomethacrylate copolymer;
resorcinol, glyoxal, AMPS/polypropylene glycol monomethacrylate copolymer;
resorcinol, glyoxylic acid, AMPS/polypropylene glycol monomethacrylate copolymer;
resorcinol, glutardialdehyde, AMPS/polypropylene glycol monoacrylate copolymer;
resorcinol, succindialdehyde, AMPS/polypropylene glycol monoacrylate copolymer;
resorcinol, glyoxal, AMPS/polypropylene glycol monoacrylate copolymer;
resorcinol, glyoxylic acid, AMPS/polypropylene glycol monoacrylate copolymer;
resorcinol, glutardialdehyde, AMPS/methoxypolyethylene glycol monomethacrylate copolymer;
resorcinol, succindialdehyde, AMPS/methoxypolyethylene glycol monomethacrylate copolymer;
resorcinol, glyoxal, AMPS/methoxypolyethylene glycol monomethacrylate copolymer;
resorcinol, glyoxylic acid, AMPS/methoxypolyethylene glycol monomethacrylate copolymer;
resorcinol, glutardialdehyde, AMPS/methoxypolyethylene glycol monoacrylate copolymer;
resorcinol, succindialdehyde, AMPS/methoxypolyethylene glycol monoacrylate copolymer;
resorcinol, glyoxal, AMPS/methoxypolyethylene glycol monoacrylate copolymer;

resorcinol, glyoxylic acid, AMPS/methoxypolyethylene glycol monoacrylate copolymer;
urea, glutardialdehyde, AMPS/hydroxyethyl methacrylate copolymer;
urea, succindialdehyde, AMPS/hydroxyethyl methacrylate copolymer;
urea, glyoxal, AMPS/hydroxyethyl methacrylate copolymer;
urea, glyoxylic acid, AMPS/hydroxyethyl methacrylate copolymer;
urea, glutardialdehyde, AMPS/hydroxyethyl acrylate copolymer;
urea, succindialdehyde, AMPS/hydroxyethyl acrylate copolymer;
urea, glyoxal, AMPS/hydroxyethyl acrylate copolymer;
urea, glyoxylic acid, AMPS/hydroxyethyl acrylate copolymer;
urea, glutardialdehyde, AMPS/hydroxypropyl methacrylate copolymer;
urea, succindialdehyde, AMPS/hydroxypropyl methacrylate copolymer;
urea, glyoxal, AMPS/hydroxypropyl methacrylate copolymer;
urea, glyoxylic acid, AMPS/hydroxypropyl methacrylate copolymer;
urea, glutardialdehyde, AMPS/hydroxypropyl acrylate copolymer;
urea, succindialdehyde, AMPS/hydroxypropyl acrylate copolymer;
urea, glyoxal, AMPS/hydroxypropyl acrylate copolymer;
urea, glyoxylic acid, AMPS/hydroxypropyl acrylate copolymer;
urea, glutardialdehyde, AMPS/hydroxybutyl methacrylate copolymer;
urea, succindialdehyde, AMPS/hydroxybutyl methacrylate copolymer;
urea, glyoxal, AMPS/hydroxybutyl methacrylate copolymer;
urea, glyoxylic acid, AMPS/hydroxybutyl methacrylate copolymer;
urea, glutardialdehyde, AMPS/hydroxybutyl acrylate copolymer;
urea, succindialdehyde, AMPS/hydroxybutyl acrylate copolymer;
urea, glyoxal, AMPS/hydroxybutyl acrylate copolymer;
urea, glyoxylic acid, AMPS/hydroxybutyl acrylate copolymer;
urea, glutardialdehyde, AMPS/polyethylene glycol monomethacrylate copolymer;
urea, succindialdehyde, AMPS/polyethylene glycol monomethacrylate copolymer;
urea, glyoxal, AMPS/polyethylene glycol monomethacrylate copolymer;
urea, glyoxylic acid, AMPS/polyethylene glycol monomethacrylate copolymer;
urea, glutardialdehyde, AMPS/polyethylene glycol monoacrylate copolymer;
urea, succindialdehyde, AMPS/polyethylene glycol monoacrylate copolymer;
urea, glyoxal, AMPS/polyethylene glycol monoacrylate copolymer;
urea, glyoxylic acid, AMPS/polyethylene glycol monoacrylate copolymer;
urea, glutardialdehyde, AMPS/polypropylene glycol monomethacrylate copolymer;
urea, succindialdehyde, AMPS/polypropylene glycol monomethacrylate copolymer;
urea, glyoxal, AMPS/polypropylene glycol monomethacrylate copolymer;
urea, glyoxylic acid, AMPS/polypropylene glycol monomethacrylate copolymer;
urea, glutardialdehyde, AMPS/polypropylene glycol monoacrylate copolymer;
urea, succindialdehyde, AMPS/polypropylene glycol monoacrylate copolymer;
urea, glyoxal, AMPS/polypropylene glycol monoacrylate copolymer;
urea, glyoxylic acid, AMPS/polypropylene glycol monoacrylate copolymer;
urea, glutardialdehyde, AMPS/methoxypolyethylene glycol monomethacrylate copolymer;
urea, succindialdehyde, AMPS/methoxypolyethylene glycol monomethacrylate copolymer;
urea, glyoxal, AMPS/methoxypolyethylene glycol monomethacrylate copolymer;
urea, glyoxylic acid, AMPS/methoxypolyethylene glycol monomethacrylate copolymer;
urea, glutardialdehyde, AMPS/methoxypolyethylene glycol monoacrylate copolymer;
urea, succindialdehyde, AMPS/methoxypolyethylene glycol monoacrylate copolymer;
urea, glyoxal, AMPS/methoxypolyethylene glycol monoacrylate copolymer;
urea, glyoxylic acid, AMPS/methoxypolyethylene glycol monoacrylate copolymer;
melamine, glutardialdehyde, AMPS/hydroxyethyl methacrylate copolymer;
melamine, succindialdehyde, AMPS/hydroxyethyl methacrylate copolymer;
melamine, glyoxal, AMPS/hydroxyethyl methacrylate copolymer;
melamine, glyoxylic acid, AMPS/hydroxyethyl methacrylate copolymer;
melamine, glutardialdehyde, AMPS/hydroxyethyl acrylate copolymer;
melamine, succindialdehyde, AMPS/hydroxyethyl acrylate copolymer;
melamine, glyoxal, AMPS/hydroxyethyl acrylate copolymer;
melamine, glyoxylic acid, AMPS/hydroxyethyl acrylate copolymer;
melamine, glutardialdehyde, AMPS/hydroxypropyl methacrylate copolymer;
melamine, succindialdehyde, AMPS/hydroxypropyl methacrylate copolymer;
melamine, glyoxal, AMPS/hydroxypropyl methacrylate copolymer;
melamine, glyoxylic acid, AMPS/hydroxypropyl methacrylate copolymer;
melamine, glutardialdehyde, AMPS/hydroxypropyl acrylate copolymer;
melamine, succindialdehyde, AMPS/hydroxypropyl acrylate copolymer;
melamine, glyoxal, AMPS/hydroxypropyl acrylate copolymer;
melamine, glyoxylic acid, AMPS/hydroxypropyl acrylate copolymer;
melamine, glutardialdehyde, AMPS/hydroxybutyl methacrylate copolymer;
melamine, succindialdehyde, AMPS/hydroxybutyl methacrylate copolymer;
melamine, glyoxal, AMPS/hydroxybutyl methacrylate copolymer;

melamine, glyoxylic acid, AMPS/hydroxybutyl methacrylate copolymer;
melamine, glutardialdehyde, AMPS/hydroxybutyl acrylate copolymer;
melamine, succindialdehyde, AMPS/hydroxybutyl acrylate copolymer;
melamine, glyoxal, AMPS/hydroxybutyl acrylate copolymer;
melamine, glyoxylic acid, AMPS/hydroxybutyl acrylate copolymer;
melamine, glutardialdehyde, AMPS/polyethylene glycol monomethacrylate copolymer;
melamine, succindialdehyde, AMPS/polyethylene glycol monomethacrylate copolymer;
melamine, glyoxal, AMPS/polyethylene glycol monomethacrylate copolymer;
melamine, glyoxylic acid, AMPS/polyethylene glycol monomethacrylate copolymer;
melamine, glutardialdehyde, AMPS/polyethylene glycol monoacrylate copolymer;
melamine, succindialdehyde, AMPS/polyethylene glycol monoacrylate copolymer;
melamine, glyoxal, AMPS/polyethylene glycol monoacrylate copolymer;
melamine, glyoxylic acid, AMPS/polyethylene glycol monoacrylate copolymer;
melamine, glutardialdehyde, AMPS/polypropylene glycol monomethacrylate copolymer;
melamine, succindialdehyde, AMPS/polypropylene glycol monomethacrylate copolymer;
melamine, glyoxal, AMPS/polypropylene glycol monomethacrylate copolymer;
melamine, glyoxylic acid, AMPS/polypropylene glycol monomethacrylate copolymer;
melamine, glutardialdehyde, AMPS/polypropylene glycol monoacrylate copolymer;
melamine, succindialdehyde, AMPS/polypropylene glycol monoacrylate copolymer;
melamine, glyoxal, AMPS/polypropylene glycol monoacrylate copolymer;
melamine, glyoxylic acid, AMPS/polypropylene glycol monoacrylate copolymer;
melamine, glutardialdehyde, AMPS/methoxypolyethylene glycol monomethacrylate copolymer;
melamine, succindialdehyde, AMPS/methoxypolyethylene glycol monomethacrylate copolymer;
melamine, glyoxal, AMPS/methoxypolyethylene glycol monomethacrylate copolymer;
melamine, glyoxylic acid, AMPS/methoxypolyethylene glycol monomethacrylate copolymer;
melamine, glutardialdehyde, AMPS/methoxypolyethylene glycol monoacrylate copolymer;
melamine, succindialdehyde, AMPS/methoxypolyethylene glycol monoacrylate copolymer;
melamine, glyoxal, AMPS/methoxypolyethylene glycol monoacrylate copolymer;
melamine, glyoxylic acid, AMPS/methoxypolyethylene glycol monoacrylate copolymer;
resorcinol, glutardialdehyde, AMPP/polyethylene glycol monomethacrylate copolymer;
resorcinol, succindialdehyde, AMPP/polyethylene glycol monomethacrylate copolymer;
resorcinol, glyoxal, AMPP/polyethylene glycol monomethacrylate copolymer;
resorcinol, glyoxylic acid, AMPP/polyethylene glycol monomethacrylate copolymer;
resorcinol, glutardialdehyde, AMPP/polyethylene glycol monoacrylate copolymer;
resorcinol, succindialdehyde, AMPP/polyethylene glycol monoacrylate copolymer;
resorcinol, glyoxal, AMPP/polyethylene glycol monoacrylate copolymer;
resorcinol, glyoxylic acid, AMPP/polyethylene glycol monoacrylate copolymer;
resorcinol, glutardialdehyde, AMPP/polypropylene glycol monomethacrylate copolymer;
resorcinol, succindialdehyde, AMPP/polypropylene glycol monomethacrylate copolymer;
resorcinol, glyoxal, AMPP/polypropylene glycol monomethacrylate copolymer;
resorcinol, glyoxylic acid, AMPP/polypropylene glycol monomethacrylate copolymer;
resorcinol, glutardialdehyde, AMPP/polypropylene glycol monoacrylate copolymer;
resorcinol, succindialdehyde, AMPP/polypropylene glycol monoacrylate copolymer;
resorcinol, glyoxal, AMPP/polypropylene glycol monoacrylate copolymer;
resorcinol, glyoxylic acid, AMPP/polypropylene glycol monoacrylate copolymer;
resorcinol, glutardialdehyde, AMPP/methoxypolyethylene glycol monomethacrylate copolymer;
resorcinol, succindialdehyde, AMPP/methoxypolyethylene glycol monomethacrylate copolymer;
resorcinol, glyoxal, AMPP/methoxypolyethylene glycol monomethacrylate copolymer;
resorcinol, glyoxylic acid, AMPP/methoxypolyethylene glycol monomethacrylate copolymer;
resorcinol, glutardialdehyde, AMPP/methoxypolyethylene glycol monoacrylate copolymer;
resorcinol, succindialdehyde, AMPP/methoxypolyethylene glycol monoacrylate-copolymer;
resorcinol, glyoxal, AMPP/methoxypolyethylene glycol monoacrylate copolymer;
resorcinol, glyoxylic acid, AMPP/methoxypolyethylene glycol monoacrylate copolymer;
phloroglucinol, glutardialdehyde, AMPP/polyethylene glycol monomethacrylate copolymer;
phloroglucinol, succindialdehyde, AMPP/polyethylene glycol monomethacrylate copolymer;
phloroglucinol, glyoxal, AMPP/polyethylene glycol monomethacrylate copolymer;
phloroglucinol, glyoxylic acid, AMPP/polyethylene glycol monomethacrylate copolymer;
phloroglucinol, glutardialdehyde, AMPP/polyethylene glycol monoacrylate copolymer;
phloroglucinol, succindialdehyde, AMPP/polyethylene glycol monoacrylate copolymer;
phloroglucinol, glyoxal, AMPP/polyethylene glycol monoacrylate copolymer;
phloroglucinol, glyoxylic acid, AMPP/polyethylene glycol monoacrylate copolymer;
phloroglucinol, glutardialdehyde, AMPP/polypropylene glycol monomethacrylate copolymer;
phloroglucinol, succindialdehyde, AMPP/polypropylene glycol monomethacrylate copolymer;
phloroglucinol, glyoxal, AMPP/polypropylene glycol monomethacrylate copolymer;
phloroglucinol, glyoxylic acid, AMPP/polypropylene glycol monomethacrylate copolymer;
phloroglucinol, glutardialdehyde, AMPP/polypropylene glycol monoacrylate copolymer;

phloroglucinol, succindialdehyde, AMPP/polypropylene glycol monoacrylate copolymer;

phloroglucinol, glyoxal, AMPP/polypropylene glycol monoacrylate copolymer;

phloroglucinol, glyoxylic acid, AMPP/polypropylene glycol monoacrylate copolymer;

phloroglucinol, glutardialdehyde, AMPP/methoxypolyethylene glycol monomethacrylate copolymer;

phloroglucinol, succindialdehyde, AMPP/methoxypolyethylene glycol monomethacrylate copolymer;

phloroglucinol, glyoxal, AMPP/methoxypolyethylene glycol monomethacrylate copolymer;

phloroglucinol, glyoxylic acid, AMPP/methoxypolyethylene glycol monomethacrylate copolymer;

phloroglucinol, glutardialdehyde, AMPP/methoxypolyethylene glycol monoacrylate copolymer;

phloroglucinol, succindialdehyde, AMPP/methoxypolyethylene glycol monoacrylate copolymer;

phloroglucinol, glyoxal, AMPP/methoxypolyethylene glycol monoacrylate copolymer; and phloroglucinol, glyoxylic acid, AMPP/methoxypolyethylene glycol monoacrylate copolymer.

The disintegrants modified according to the present invention are compounds and materials which expand or release gases on an elevation in temperature to a defined temperature range and thus build up the pressure required within the capsule to disintegrate the shell of the microcapsule. In order to build up a high pressure, it can be advantageous to use compounds which have a very low boiling point or which participate in a chemical reaction or decomposition with release of gases in a defined temperature range. Such compounds are known to those skilled in the art.

It can be advantageous to select the disintegrant so that the expansion, the chemical reaction, or decomposition thereof with release of gases takes place in the previously defined temperature range.

In an embodiment of the present invention, more than 50%, for example, more than 70%, for example, more than 80%, of the capsules open in a temperature interval of at most 20° C., for example, in an interval of at most 10° C., for example, of at most 5° C. The active ingredient is thereby released from the microcapsules in a desired temperature range. This is desirable, for example, in the use of flame retardants, or in chemical processes and syntheses, when a release, e.g., of catalysts, is necessary or desirable after a defined temperature is reached. A further effect is that an active ingredient can be introduced encapsulated to the point of its use and first released there by heating to the opening temperature. A further advantage of the microcapsule according to the present invention is that polymers and copolymers that are stable and known to those skilled in the art can be used for the shell of the microcapsules. A system is created thereby which, with the wall material for disintegrants remaining constant, adapts to the application, and not the wall material. This means a high flexibility with low costs. Selecting suitable disintegrants which are introduced into the microcapsules in surface-modified form according to the invention leads to the microcapsules, in a particular embodiment of the present invention, already opening at a temperature of below 150° C., for example, of below 120° C., for example, below 100° C. An embodiment of the present invention is a microcapsule which opens in a temperature range of 80-120° C., or 60-70° C. The microcapsules of the prior art, i.e., microcapsules without disintegrant, in contrast, frequently do not open until temperatures of about 200° C.

Disintegrants in the context of the present invention are therefore, in particular, also compounds which under the influence of temperature release gases, and also particles which contain a blowing agent. As disintegrants, compounds are suitable which release nitrogen ($N_2$) or carbon dioxide ($CO_2$). Other compounds which, under the influence of temperature, in a defined temperature range, release non-toxic gases such as neon, argon, vaporous water, low-molecular-weight hydrocarbons or halogenated hydrocarbons, are also suitable for the present invention.

Those which are particularly suitable are sodium hydrogencarbonate, sodium carbonate, potassium carbonate, potassium hydrogencarbonate, azodicarbonamides, hydrazides, such as, for example, p-toluenesulphonyl hydrazide, carbazides, such as, for example, 4,4-oxy-bis(benzosulphohydrazide), and 2,2-toluylenesulphonyl semicarbazide, tetrazoles, such as, for example, 5-phenyltetrazole and/or citric acid derivatives.

In an embodiment of the present invention, the disintegrant of the microcapsule according to the present invention, can, for example, be selected from the group consisting of: sodium hydrogencarbonate, sodium carbonate, potassium carbonate, potassium hydrogencarbonate, azodicarbonamide, p-toluenesulphonyl hydrazide, 4,4-oxy-bis(benzosulphohydrazide), 2,2-toluylenesulphonyl semicarbazide, 5-phenyltetrazole and/or citric acid derivatives.

Table 1 lists examples of some advantageous disintegrants, the decomposition temperatures thereof, the gases formed thereof on decomposition, and also the gas yield.

TABLE 1

Various Disintegrants

| Name | Decomposition Temp. (° C.) | Gas yield (ml/g) | Gases |
|---|---|---|---|
| Azodicarbonamide | 200-300 | 280-320 | $N_2$, CO, ($NH_3$, $CO_2$) |
| p-Toluenesulphonyl hydrazide | 110-140 | 120-140 | $N_2$, $H_2O$ |
| 4,4-Oxy-bis(benzosulphohydrazide) | 140-165 | 120-150 | $N_2$, $H_2O$ |
| 2,2-Toluylenesulphonylsemicarbazide | 215-235 | 120-140 | $N_2$, $CO_2$ |
| 5-Phenyltetrazole | 240-250 | 190-210 | $N_2$ |
| Sodium hydrogencarbonate | 120-150 | 130-170 | $CO_2$, $H_2O$ |
| Citric acid derivates | 200-220 | 90-120 | $CO_2$, $H_2O$ |

Particles which are particularly suitable as disintegrants in the context of the present invention contain a blowing agent, expand owing to a temperature increase, and can, for example, consist substantially of a polymer sheath and a gaseous or liquid core, for example, they consist of a polymer sheath and a core. In this case the polymer can be a polymer or copolymer. Examples of suitable polymers are the following which are known to those skilled in the art: polyethylene (PE), polyurethane (PU), polypropylene (PP), polyvinyl chloride (PVC), polymethyl methacrylate (PMMA), polyvinylidene dichloride (PVDC), polyacrylonitrile (PAN), polyvinylidene dichloride-acrylonitrile copolymer and poly(meth)acrylate. Suitable gaseous expandable blowing agents are nitrogen, carbon dioxide, and also low-molecular-weight hydrocarbons and low-molecular-weight halogenated hydrocarbons. Examples of low-molecular-weight hydrocarbons are isobutan and isopentan. Examples of suitable liquid expandable blowing agents are low-molecular-weight hydrocarbons and low-molecular-weight halogenated hydrocarbons having a low boiling point in the range from 40 to 150° C., for example, 50 to 130, and, for example, in the range of from 60 to 120° C.

The average size of such expandable particles is between 5 and 50 μm, for example, between 10 and 40 μm, and, for example, between 15 and 35 μm. The volume of the particles can, for example, grow on expansion by 50 fold to 100 fold.

An embodiment of the disintegrants according to the present invention are expandable particles comprising a sheath of polymethyl methacrylate (PMMA) and/or an alkyl polyacrylate having a wall thickness of 2 to 15 micrometers, a core made of a liquid or gaseous hydrocarbon having a boiling point in the range from 40 to 150° C., for example, 50 to 130, and, for example, in the range from 60 to 120° C., and having a diameter of the microcapsule in the range of between 5 and 50 μm, for example, between 10 and 40 μm, and, for example, between 15 and 35 μm.

Suitable particles of this type are commercially available and can be obtained, for example, under the trade name Expancel® from AkzoNobel and also under the trade name Matsumoto® Microspheres (F and FN Series) from Matsumoto Yushi-Seiyaku Co., Ltd. (Japan). Examples of suitable particles are Expancel® 007 WUF 40, Expancel® 920 WUF 40, Expancel® 461 DU 40, Expancel® 053 WO 40, and Matsumoto® Microsphere F 36.

The Expancel® DU (dry unexpanded) types from Akzo Nobel, differ essentially in their size (6 to 45 μm in diameter in the unexpanded state) and the temperature required for starting the expansion (75 to 220° C.). Other unexpanded particle types are furthermore available as aqueous dispersions having a particle fraction of about 40 to 45 wt.-%. Particles are furthermore available as polymer-bound particles (masterbatches), for example, ethylene-vinyl acetate with a particle concentration of about 65 wt %. The particle dispersions and the masterbatches are as suitable as the DU types of foaming of adhesives according to the method of the invention.

Heating of the particles softens the outer polymer shell and transfers the liquid core material into its gaseous state. The particles thus expand irreversibly in three dimensions. The expansion is completed when the internal and external pressure equalize each other. Since the polymeric shell remains intact, a foam with closed cells is obtained.

According to the present invention, the disintegrants for the encapsulation process, that is to say, for the in situ production of microcapsules, are surface-modified in advance. It is thereby possible to encapsulate the disintegrant efficiently together with the core material and the active ingredient.

In an embodiment of the present invention, the disintegrant can, for example, be modified so that it has a zeta potential in the range from −0.9 to 0.8 mV, for example, in the range from −0.9 to −0.01 mV, or in the range from 0.01 to 0.8 mV, or in the range from −0.3 to 0.4 mV. The zeta potential is measured as electrophoretic mobility (see below).

The surface modification of the disintegrant that is to be encapsulated can be determined via the zeta potential known to those skilled in the art. The zeta potential (ζ-potential) describes the electric potential (also termed Coulomb potential) at the slipping plane of a moving particle in a suspension. The electric potential describes the ability of a field caused by the charge to exert force on other charges. The zeta potential gives information on the degree of repulsion between adjacent particles of like charge in a suspension.

The zeta potential cannot be measured directly, but can be calculated on the basis of theoretical models and the experimentally determined electrophoretic mobility or the dynamic electrophoretic mobility (EM). One example of the determination of electrophoretic mobility is described hereinafter.

Electrophoresis serves for estimating zeta potentials of particles, wherein a flow potential/stream is used for porous bodies and flat surfaces. The EM is usually determined by applying an electric field to a dispersion. Particles within the dispersion having a zeta potential then move to the oppositely charged electrode at a velocity which is proportional to the order of magnitude of the EM and thereby permits conclusions to be drawn of the zeta potential. The velocity is usually measured using a laser-Doppler anemometer. The frequency shift or the phase shift of an exciting laser beam through the moving particles is measured as the particle mobility which then is converted to the zeta potential using the viscosity of the dispersion medium and the dielectric permittivity.

For use in the customary oil-in-water encapsulations, it can be advantageous to hydrophobize the surface of the disintegrant, that is to say, to finish it so that the surface is likewise hydrophobic in accordance with the hydrophobic active ingredient of the core material so that the disintegrant can be encapsulated with the hydrophobic active ingredient(s) to give the microcapsules according to the present invention. The surface treatment thereby leads to a compatibility of disintegrants and core material. This compatibility permits an effective encapsulation. In an embodiment of the present invention, therefore, the surface of the disintegrant can, for example, be hydrophobized. Compounds used for hydrophobizing the disintegrant are referred to as hydrophobizing agents.

A surface modification, in particular hydrophobization of the surface, according to the present invention of the disintegrant and therefore the setting of a defined zeta potential, can, for example, be achieved in that the surface of the disintegrant is treated with at least one compound from the group consisting of polyethylene imides, quaternary ammonium compounds, quaternary polyvinyl pyrrolidones and oleic acid, and also preparations thereof in organic solvents, such as, e.g., n-butanol, 1,4-butanediol, ethylene glycol or water.

In an embodiment of the present invention, the surface of the disintegrant used according to the present invention can, for example, be modified with a compound selected from the group consisting of polyethylene imides, quaternary ammonium compounds, quaternary polyvinyl pyrrolidones and oleic acid, that is to say, is hydrophobized.

Examples of quaternary ammonium compounds are betaine, choline chloride, benzalkonium chloride and also didecyldimethylammonium chloride. Commercially available ammonium compounds and also preparations of ammonium compounds can also advantageously be used in the present invention for modification of disintegrant surfaces. Examples thereof are Lanco Stat L 80 N, Lanco Stat LI 100, Lanco Stat PUN and Lanco Stat FN from Lubrizol Deutschland GmbH.

Suitable polyethylene imide compounds are multifunctional cationic polymers based on ethylene imide having molar masses in the range from 600 to 2 500 000 Da. Such polyethylene imides and preparations thereof are commercially available, for example, under the trade name Lupasol from BASF SE (Germany).

Quaternary polyvinyl pyrrolidones which can likewise advantageously be used in the present invention are obtainable, for example, under the trade name Luviquat from BASF SE (Germany).

According to an embodiment of the present invention, the surface of the disintegrant can, for example, be modified with a siloxane compound as hydrophobizing agent. Siloxane compounds are highly efficient hydrophobizing agents.

Examples of siloxane compounds as hydrophobizing agents according to the present invention are Tego® Phobe 1500N, Tego® Phobe 1505, Tego® Phobe 1401 and Tego® Phobe 6010.

Tego® Phobe 1500 N is β-(3,4-Epoxycyclohexyl)-ethyl-triethoxysilane, 50 wt.-% in the solvent tripropylenglycol-monomethylether and Isoparaffin-carbohydrats C10-C13 in a ratio of 40:10.

Tego® Phobe 1505 is a preparation on the basis of amino functional polysiloxane, 85 wt.-% in the solvent isopropyl-laurat. Tego® Phobe 1401 is a further siloxane hydrophobizing agent. Tego® Phobe 6010 is a low molecular modified polysiloxane resin.

Further examples of hydrophobizing agents according to the present invention are Ceretan® WE 0825, Deurex E09K, Codamide VRX Powder, Eicosan ($C_{20}H_{42}$), Disperbyk 180, Disperbyk 2022, Deurex X51, Deurex V2.

Ceretan® WE 0825 is an unpolar polyethylene with a drop point of 110 to 118° C. Deurex E09K is a unipolar hard polyethylene wax with a drop point of 110° C. Codamide VRX Powder is an oleic acid amide. Disperbyk 180 is an alkyl ammonium salt of a copolymer with seidic groups. Disperbyk 2022 is a structured copolymer as a 60% solution in 2-metoxy-propylacetat. Deurex X51 is a raw sugar cane wax. Deurex V2 is a vinylether wax, with a drop point of 48° C.

Examples of hydrophobizing agents are summarized in Table 2.

TABLE 2

List of Hydrophobizing Agents

| Name | Description |
|---|---|
| Ceretan ® WE 0825 | unpolar polyethylene, Drop point 110-118 |
| Deurex ® E09K | unpolar hard polyethylene-wax, Drop point 110° C. |
| Crodamide ® VRX Powder | Oleic acid amide, CAS-No. 301-02-0 |
| Oleic acid | |
| Eicosan | $C_{20}H_{42}$ |
| Tego ® Phobe 1500 N | β-(3,4-epoxycyclohexyl)ethyltriethoxy silane, content 50 wt.-% in the solvent dipropylenglycol monomethyl ether/isoparaffin hydrocarbon $C_{10}$-$C_{13}$ (40:10) |
| Tego ® Phobe 1505 | Preparation on the basis of an amino functional Polysiloxans, content of active ingredient about 85%, solvent isopropyl laurate |
| Tego ® Phobe 1401 | Siloxane hydrophobizing agent |
| DISPERBYK 180 | Alkylol ammonium salt of a copolymer with acidic groups |
| DISPERBYK ® 2022 | structured Copolymer, concentration 60 wt.-% in the solvent 2-Methoxypropylacetat |
| Deurex ® X51 | raw sugar cane wax, in policosanol, a mixture of eight aliphatic alcohols |
| Deurex ® V2 | polyvinyl ether, Drop point: 48° C. |
| Tego ® Phobe 6010 | low molecular, modified polysiloxane resin |
| Dynasylan ® Octeo | monomeric medium-chain alkyl-functional silane |

Examples of combinations of core/sheath disintegrants and hydrophobizing agents are set forth in Table 3.

TABLE 3

Combinations of Core/Sheath Disintegrants and Hydrophobizing Agents

| Disintegrant | Hydrophobizing Agent |
|---|---|
| Expancel ® 007 WUF 40 | Oleic acid |
| Expancel ® 920 WUF 40 | Oleic acid |
| Expancel ® 461 DU 40 | Crodamide ® VRX Powder |
| Expancel ® 461 DU 40 | Ceretan ® WE 0825 |
| Expancel ® 461 DU 40 | Deurex ® X51 |
| Expancel ® 007 WUF 40 | Crodamide ® VRX Powder |
| Expancel ® 007 WUF 40 | Ceretan ® WE 0825 |
| Expancel ® 007 WUF 40 | Deurex ® X51 |
| Expancel ® 920 WUF 40 | Ceretan ® WE 0825 |
| Expancel ® 920 WUF 40 | Oleic acid |
| Expancel ® 007 WUF 40 | Crodamide ® VRX Powder |
| Expancel ® 920 WUF 40 | Deurex ® X51 |
| Expancel ® 007 WUF 40 | Eicosan |
| Expancel ® 461 DU 40 | Ceretan ® WE 0825 |
| Expancel ® 461 DU 40 | Eicosan |
| Expancel ® 007 WUF 40 | Eicosan |
| Expancel ® 007 WUF 40 | DISPERBYK ® 180 |
| Expancel ® 007 WUF 40 | DISPERBYK ® 2022 |
| Expancel ® 007 WUF 40 | Tego ® Phobe 1505 |
| Expancel ® 007 WUF 40 | Dynasylan ® OCTEO |
| Expancel ® 007 WUF 40 | Tego ® Phobe1500N |
| Matsumoto ® Microsphere F 36 | Tego ® Phobe1401 |
| Matsumoto ® Microsphere F 36 | Dynasylan ® OCTEO |
| Matsumoto ® Microsphere F 36 | Tego ® Phobe1505 |
| Matsumoto ® Microsphere F 36 | Deurex ® V2 |

In an embodiment of the present invention, the fraction of the surface-treated, in particular hydrophobized, disintegrants can, for example, be between 0.1 and 90% by weight of the core material.

In an embodiment of the present invention, the fraction of the surface-treated, in particular hydrophobized, disintegrants of the core material that is to be encapsulated can, for example, be between 0.1% by weight and 90%, for example, between 10% and 80% by weight, and, for example, between 20% and 70% by weight, based on the total weight of the core material of the microcapsules according to the invention.

In an embodiment of the present invention, the percentage of the surface-treated, in particular hydrophobized, disintegrant in the core material can, for example, be in the range from 0.1 wt.-% and 30 wt.-%. The percentage of the surface-treated, in particular hydrophobized, disintegrant in the core material can, for example, be in the range from 10 wt.-% and 20 wt.-%.

The microcapsules according to the present invention can, for example, be produced by a multistage method. In this case, the surface of the disintegrant or disintegrants is first modified according to the present invention. For this purpose, the at least one disintegrant is suspended in water together with one or more of the abovementioned modification agents. Alternatively thereto, the modification agent can also be added to an aqueous suspension of the disintegrant, or the disintegrant can be suspended in a solution or suspension of the modification agent. The disintegrant can, for example, then be dried. The surface-modified disintegrant can, for example, be filtered off, filtered off by suction or separated off from the suspension by means of centrifugation, and dried at a suitable temperature and/or in vacuum.

For the hydrophobic treatment of the disintegrant, in particular the disintegrants formed by a core and a sheath (core/sheath disintegrant) may be dried before. It is necessary that this optional drying step is carried out at a temperature below the starting temperature of the disintegrant. The starting temperature of the disintegrant according to the present invention is the temperature in which the disintegration reaction starts. The starting temperature may be identical to the expansion temperature of the core/sheath disintegrant. In particular the starting temperature is lower than the expansion temperature.

Disintegrant and hydrophobizing agent may be combined in a ratio in the range from 500:1 to 1:50. The disintegrant and the hydrophobizing agent can, for example, be added in a ratio in the range from 300:1 to 1:1, for example, in a ratio in the range from 80:1 to 1:1. In an embodiment, the ratio can, for example, be in the range from 250:1 to 10:1. The disintegrant and the hydrophobizing agent can, for example, be added in a ratio from 200:1 to 20:1.

As described above, one option for the hydrophobic treatment is the dispersion of the disintegrant in a solvent to which the hydrophobizing agent is then added. During addition of the hydrophobizing agent the dispersion can, for example, be stirred. The stirring speed may, for example, be in a range from 50 rpm to 5,000 rpm. The stirring speed is in the range from 100 rpm to 1,000 rpm. The stirring speed can, for example, be in the range from 300 to 700 rpm. In particular the stirring speed is in the range from 400 to 600 rpm. After addition, the stirring is continued for a time in the range from 2 min to 1 h, for example, in the range from 5 min to 30 min, for example, in the range from 10 to 20 min. The disintegrants solvent hydrophobizing agent mixture can, for example, be stirred for 15 min. In order to remove the solvent, the solvent may be evaporated. For example, the solvent is evaporated at room temperature. Alternatively the solvent may be evaporated in a recirculated air drying oven.

The present invention therefore further relates to a surface-modified disintegrant comprising a disintegrant selected from the group consisting of substances which release gases under the influence of temperature, and microcapsules which contain a blowing agent, wherein the surface of the disintegrant is hydrophobized.

The surface-modified disintegrant obtained in this manner is then dispersed in the active ingredient or together with the active ingredient of the core material and then, in a method known to those skilled in the art, is encapsulated with the shell material to give the microcapsules according to the present invention.

In an embodiment of the present invention, the microcapsule can, for example, comprise a shell formed by phloroglucin and glutaraldehyde, and a core comprising a disintegrant consisting of an expandable particle comprising a particle sheath of PMMA and a particle core made of a liquid or gaseous hydrocarbon having a boiling point in the range from 40 to 150° C., wherein the particle sheath has been hydrophobized by a siloxane compound.

In an embodiment of the present invention, the microcapsule can, for example, comprise a shell formed by phloroglucin and glutaraldehyde, and a core comprising a disintegrant consisting of an expandable particle comprising a particle sheath of polyacrylonitrile and a particle core made of a liquid or gaseous hydrocarbon having a boiling point in the range from 40 to 150° C., wherein the particle sheath has been hydrophobized by a siloxane compound.

In an embodiment of the present invention, the microcapsule can, for example, comprise a shell formed by phloroglucin and glutaraldehyde, and a core comprising a disintegrant consisting of an expandable particle comprising a particle sheath of PMMA and a particle core made of a liquid or gaseous hydrocarbon having a boiling point in the range from 40 to 150° C., wherein the particle sheath has been hydrophobized by Tego® Phobe 1500N, Tego® Phobe 1505, Tego® Phobe 1401 or Tego® Phobe 6010.

In an embodiment of the present invention, the microcapsule can, for example, comprise a shell formed by phloroglucin and glutaraldehyde, and a core comprising a disintegrant consisting of an expandable particle comprising a particle sheath of polyacrylonitrile and a particle core made of a liquid or gaseous hydrocarbon having a boiling point in the range from 40 to 150° C., wherein the particle sheath has been hydrophobized by Tego® Phobe 1500N, Tego® Phobe 1505, Tego® Phobe 1401 or Tego® Phobe 6010.

In an embodiment of the present invention, the microcapsule can, for example, comprise a shell formed by melanin and formaldehyde, and a core comprising a disintegrant consisting of an expandable particle comprising a particle sheath of PMMA or polyacrylonitrile and a particle core made of a liquid or gaseous hydrocarbon having a boiling point in the range from 40 to 150° C., wherein the particle sheath has been hydrophobized by a siloxane compound.

In an embodiment of the present invention, the microcapsule can, for example, comprise a shell formed by melanin and formaldehyde, and a core comprising a disintegrant consisting of an expandable particle comprising a particle sheath of polyacrylonitrile and a particle core made of a liquid or gaseous hydrocarbon having a boiling point in the range from 40 to 150° C., wherein the particle sheath has been hydrophobized by a siloxane compound.

In an embodiment of the present invention, the microcapsule can, for example, comprise a shell formed by melanin and formaldehyde, and a core comprising a disintegrant consisting of an expandable particle comprising a particle sheath of PMMA and a particle core made of a liquid or gaseous hydrocarbon having a boiling point in the range from 40 to 150° C., wherein the particle sheath has been hydrophobized by Tego® Phobe 1500N, Tego® Phobe 1505, Tego® Phobe 1401 or Tego® Phobe 6010.

In an embodiment of the present invention, the microcapsule can, for example, comprise a shell formed by melanin and formaldehyde, and a core comprising a disintegrant consisting of an expandable particle comprising a particle sheath of polyacrylonitrile and a particle core made of a liquid or gaseous hydrocarbon having a boiling point in the range from 40 to 150° C., wherein the particle sheath has been hydrophobized by Tego® Phobe 1500N, Tego® Phobe 1505, Tego® Phobe 1401 or Tego® Phobe 6010.

Methods for producing microcapsules and also microcapsules are described in WO 2011/110368 A2, WO 2009/015872 A1, and WO 2010/102830 A2.

Methods for producing melamine-formaldehyde capsules are known to those skilled in the art, i.e, from EP-A-0415273, EP-A-0218887, EP-A-0026914 and WO-A-01/51197.

The present invention therefore further relates to a method comprising the steps (i) modification, in particular hydrophobization, of the surface of a disintegrant, and (ii) reaction of the surface-modified disintegrant with the core material, comprising at least one active ingredient, and a shell material to give the microcapsules according to the present invention.

In the method according to the present invention. the disintegrant is in particular hydrophobized before addition to the core material. The preparation of the core material is thus at least a two-step method: step a) hydrophobizing the disintegrant and step b) dispersing the disintegrant in the core material.

It was surprisingly found that with specific hydrophobizing agents, such as siloxane compounds, an in situ hydrophobic treatment is possible. "In situ hydrophobic treatment" according to the present invention is a hydrophobic treatment in the core material that is later incapsulated in the microcapsules according to the present invention. In this specific treatment method, both the disintegrant and the hydrophobizing agent interact within the core material.

For example, a mixture of the core material, i.e., an oil and the hydrophobizing agent, is added into a beaker and stirred at a stirring speed. The stirring speed can be in the range from 300 to 1,000 rpm, for example, in a range from 400 to 800 rpm. The first stirring time can be in the range from 20 seconds to 10 min, for example, in the range from 1 to 5 min, or, for example, in the range from 1 to 3 min. To this mixture, the disintegrant, e.g., a core/sheath disintegrant, is added to the mixture and the stirring speed is increased to a second stirring speed. The second stirring speed can be in the range from 1,500 to 5,000 rpm, for example, in the range from 2,000 to 4,000 rpm, in particular in the range from 2,500 to 3,500 rpm. The stirring time can be in the range from 2 min to 30 min, for example, in the range from 5 min to 15 min, or, for example, in the range from 8 to 12 min. To this mixture, a precondensate for the formation of the microcapsule shell is then added. All reaction steps may thus be carried out in the same vessel. A more efficient and more economic production process of microcapsules with disintegrants is accordingly provided.

However, in situ hydrophobic treatment is only possible with highly efficient hydrophobizing agents such as a siloxane compound. Moreover, the siloxane compound has to be in a sufficient concentration in the core material. The siloxane compound can, for example, be present in the core material in a range from 0.1 wt.-% to 20 wt.-%, for example, in a range from 0.2 wt.-% to 15 wt.-%, for example, in a range from 0.5 to 10 wt.-%, for example, in a range from 0.5 to 4 wt.-%.

The present invention further relates to a microcapsule obtainable by (i) modification, in particular hydrophobization, of the surface of a disintegrant, and (ii) reaction of the surface-modified disintegrant with a core material, comprising at least one active ingredient, and a shell material.

The microcapsule according to the present invention may therefore be caused to open, and therefore to release in a targeted manner the active ingredients of the core material, by a suitable choice of disintegrant and surface modification in a temperature range defined in advance.

The microcapsule is therefore outstandingly suitable for targeted use in releasing fragrances in the textile industry, for releasing fragrances and/or hair care and/or skin care products in cosmetics, for releasing catalysts in polymer synthesis or chemical synthesis, and also for releasing lubricants in the car and mechanical engineering industries.

The present invention further relates to the use of microcapsules or microcapsule dispersions according to the invention for the controlled release of core materials, which can be hydrophilic (e.g., aroma substances) or hydrophobic. The core materials are, for example, active ingredients which can, for example, be selected from the group of fragrance and aroma substances, pesticides, herbicides, lubricants, slip agents (e.g., fluorinated hydrocarbons), insecticides, antimicrobial active ingredients, pharmaceutical active ingredients, cosmetic active ingredients (e.g., for shampoo), latent heat stores (e.g., waxes), catalysts (e.g., organic carbonates, organometallic compounds, metallocenes and the like), self-repairing agents (e.g., norbornene, dicyclopentadiene), coating systems such as paints (e.g., fragrance paints), dyes (e.g., for carbon-free self-copy systems), hydrophobic waxes, hydrophobic En-components or hydrophobic solvents.

The capsules according to the present invention may in addition be used for the addition of catalysts or initiators to coating compounds or impregnating resins. During the impregnation or coating of substrates, reactions occur, depending on the temperature, with these added reactive components which greatly modify, e.g., the viscosity of the impregnating baths. Since, frequently, subsequent thermal drying steps or thermal crosslinking reactions are desired, it is particularly desired that these catalysts are provided in a sufficient amount at certain temperatures. The capsules of the present invention that open thermally in a targeted manner therefore lead to improved control and metering, to production of novel polymer chains in initiator-started polymerizations, or to using coloring or active-ingredient-releasing systems under a certain temperature influence. This procedure is comprehensively usable, since temperature elevation and temperature adjustment are the most important method step in production technology.

However, any desired other substances are possible which can be encapsulated using the selected microcapsule system. These substances, in the context of the present invention, are summarized as "active ingredients".

The active ingredient can therefore be identical to the core material.

The inventors have additionally found that certain components core materials negatively affect the disintegrants, in particular core/sheath disintegrants as defined above. For example, the core material may include destabilizing agents that lead to a destabilization of the sheath of the disintegrants. Examples of destabilizing agents are plasticizers and polymer solvents. "Plasticizers" according to the present invention are additives that increase the plasticity or fluidity of a material. Plasticizers modify the thermal elastic range of a material towards lower temperatures. In case of an external plasticization, plasticizer is not covalently bound to the polymer but only acts on the polymer via its polar groups and accordingly increases the chain dynamics. Examples of such plasticizers are diethylhexylphtalat (DEHP), Mesamol, Hexamol, DINCH and adipinic acid based plasticizers. It is assumed that the interactions of the plasticizer with the polymer lead to expansion of the meshes of the polymeric network which leads to a swelling of the polymer. Polymer solvents according to the invention are solvents that are able to solubilize polymeric resin. The polymeric solvents are believed to attack the sheath in a similar way as described for the disintegrant. Polymeric solvents that negatively affect disintegrants according to the present invention are in particular selected from toluene, acetone, methylene chloride, chloroform, dimethylformamide (DMF), dimethylsulfoxide (DMSO), ethyl acetate.

The effect of the destabilizing agents is a strong destabilization of the sheath of the disintegrant causing a non-functionality of disintegrant. Already after a short time, as shown in Example 8, no expansion and no disintegration of the outer microcapsule can be achieved.

Core materials according to the present invention that contain destabilizing agents include perfume oils or fragrance oils. In the context of the present invention, the terms "fragrance oil(s)" and "perfume oil(s)" are used synonymously. They in particular mean any substances or their mixtures that are perceived by humans and animals as an odor, in particular by humans as a pleasant odor.

Perfume oils or constituents of perfume oils can be employed as the fragrant components. According to the present invention, perfume oils or fragrances can be individual fragrant compounds, for example, the synthetic products of the ester, ether, aldehyde, ketone, alcohol and hydrocarbon type. Fragrant compounds of the ester type are, for example, benzyl acetate, phenoxyethyl isobutyrate, p-tert.- butylcyclohexyl acetate, linalyl acetate, dimethylbenzyl carbinyl acetate (DMBCA), phenylethyl acetate, benzyl acetate, ethylmethylphenyl glycinate, allylcyclohexyl propionate, styrallyl propionate, benzyl salicylate, cyclohexyl salicylate, floramate, melusate and jasmecyclate. The ethers include, for example, benzyl ethyl ether and ambroxan; the aldehydes include, for example, the linear alkanals containing 8 to 18 carbon atoms, citral, citronellal, citronellyloxyacetaldehyde, cyclamen aldehyde, lilial and bourgeonal; the ketones include, for example, the ionones, alpha-isomethyl ionone and methyl cedryl ketone; the alcohols include anethol, citronellol, eugenol, geraniol, linalool, phenylethyl alcohol and terpineol and the hydrocarbons include, in particular the terpenes, such as limonene and pinene. Mixtures of various fragrant substances, which together produce an attractive fragrant note can, for example, be used.

Perfume oils such as these may also contain natural mixtures of fragrant substances, as are obtainable from vegetal sources, for example, pine, citrus, jasmine, patchouli, rose or ylang-ylang oil. Also suitable are muscatel sage oil, chamomile oil, clove oil, melissa oil, mint oil, cinnamon leaf oil, lime blossom oil, juniper berry oil, vetivert oil, olibanum oil, galbanum oil and laudanum oil as well as orange blossom oil, neroli oil, orange peel oil and sandalwood oil.

The volatility of a fragrant substance is important for its perceptibility, whereby in addition to the nature of the functional groups and the structure of the chemical compound, the molecular weight also plays an important role. The majority of fragrant substances thus have molecular weights up to about 200 Dalton, whereas molecular weights of 300 Dalton and above are quite an exception.

Due to the different volatilities of fragrant substances, the smell of a perfume or fragrance composed of a plurality of fragrant substances changes during evaporation, the impressions of odor being subdivided into the "top note", "middle note" or "body" and "end note" or "dry out". As the perception of smell also depends to a large extent on the intensity of the odor, the top note of a perfume or fragrance consists not solely of highly volatile compounds, whereas the end note consists to a large extent of less volatile, i.e., tenacious fragrant substances. In the composition of perfumes, higher volatile fragrant substances can be bound, for example, onto particular fixatives, whereby their rapid evaporation is impeded. In the following subdivision of fragrant substances into "more volatile" or "tenacious" fragrant substances, nothing is mentioned about the odor impression and further, whether the relevant fragrant substance is perceived as the top note or body note. Exemplary tenacious odorous substances that can be used in the context of the present invention are the ethereal oils such as angelica root oil, aniseed oil, arnica flowers oil, basil oil, bay oil, bergamot oil, champax blossom oil, silver fir oil, silver fir cone oil, elemi oil, eucalyptus oil, fennel oil, pine needle oil, galbanum oil, geranium oil, ginger grass oil, guaiacum wood oil, Indian wood oil, helichrysum oil, ho oil, ginger oil, iris oil, cajuput oil, sweet flag oil, camomile oil, camphor oil, Canoga oil, cardamom oil, cassia oil, Scotch fir oil, copaiba balsam oil, coriander oil, spearmint oil, caraway oil, cumin oil, lavender oil, lemon grass oil, limette oil, mandarin oil, melissa oil, amber seed oil, myrrh oil, clove oil, neroli oil, niaouli oil, olibanum oil, orange oil, origanum oil, Palma Rosa oil, patchouli oil, Peru balsam oil, petit grain oil, pepper oil, peppermint oil, pimento oil, pine oil, rose oil, rosemary oil, sandalwood oil, celery seed oil, lavender spike oil, Japanese anise oil, turpentine oil, thuja oil, thyme oil, verbena oil, vetiver oil, juniper berry oil, wormwood oil, wintergreen oil, ylang-ylang oil, ysop oil, cinnamon oil, cinnamon leaf oil, citronella oil, citrus oil and cypress oil. However, in the context of the present invention, the higher boiling or solid fragrant substances of natural or synthetic origin can be used as tenacious fragrant substances or mixtures thereof, namely fragrances. These compounds include the following compounds and their mixtures: ambrettolide, a-amyl cinnamaldehyde, anethol, anisaldehyde, anis alcohol, anisole, methyl anthranilate, acetophenone, benzyl acetone, benzaldehyde, ethyl benzoate, benzophenone, benzyl alcohol, benzyl acetate, benzyl benzoate, benzyl formate, benzyl valeriate, borneol, bornyl acetate, a-bromostyrene, n-decyl aldehyde, n-dodecyl aldehyde, eugenol, eugenol methyl ether, eucalyptol, farnesol, fenchone, fenchyl acetate, geranyl acetate, geranyl formate, heliotropin, methyl heptynecarboxylate, heptaldehyde, hydroquinone dimethyl ether, hydroxycinnamaldehyde, hydroxycinnamyl alcohol, indole, irone, isoeugenol, isoeugenol methyl ether, isosafrol, jasmone, camphor, carvacrol, carvone, p-cresol methyl ether, coumarone, p-methoxyacetophenone, methyl-n-amyl ketone, methylanthranilic acid methyl ester, p-methyl acetophenone, methyl chavicol, p-methyl quinoline, methyl-beta-naphthyl ketone, methyl-n-nonyl acetaldehyde, methyl-n-nonyl ketone, muscone, beta-naphthol ethyl ether, beta-naphthol methyl ether, nerol, nitrobenzene, n-nonyl aldehyde, nonyl alcohol, n-octyl aldehyde, p-oxyacetophenone, pentadecanolide, beta-phenylethyl alcohol, phenyl acetaldehyde dimethyl acetal, phenyl acetic acid, pulegone, safrol, isoamyl salicylate, methyl salicylate, hexyl salicylate, cyclohexyl salicylate, santalol, scatol, terpineol, thymine, thymol, gamma-undecalactone, vanillin, veratrum aldehyde, cinnamaldehyde, cinnamyl alcohol, cinnamic acid, ethyl cinnamate, benzyl cinnamate.

The readily volatile fragrant substances particularly include the low boiling fragrant substances of natural or synthetic origin that can be used alone or in mixtures. Exemplary readily volatile fragrant substances are alkyl isothiocyanates (alkyl mustard oils), butanedione, limonene, linalool, linalyl acetate and linalyl propionate, menthol, menthone, methyl n-heptenone, phellandrene, phenyl acetaldehyde, terpinyl acetate, citral, citronellal.

Examples of fragrant compounds of the aldehyde type are hydroxycitronellal (CAS 107-75-5), helional (CAS 1205-17-0), citral (5392-40-5), bourgeonal (18127-01-0), triplal (CAS 27939-60-2), ligustral (CAS 68039-48-5), vertocitral (CAS 68039-49-6), florhydral (CAS 125109-85-5), citronellal (CAS 106-23-0), citronellyloxyacetaldehyde (CAS 7492-67-3).

Examples of fragrance oils with a destabilizing effect include Fougere Cap, Detergaflor II and Apple-Cinnamon.

Fougere Cap contains the following major components:
10-20 wt.-% 3a,4,5,6,7a-Hexahydro-4,7-methano-1H-indenyl acetate (EINECS 259-367-2)
10-20 wt.-% Allyl heptanoate (EINECS 205-527-1)
5-10 wt.-% Bornan-2-on (EINECS 200-945-0)
5-10 wt.-% Linalyl acetate (EINECS 204-116-4)
5-10 wt.-% Dimethylcyclohex-3-ene-1-carbaldehyde (EINECS 248-742-6)

Detergaflor II contains the following major components:
10-25 wt.-% Dihydromyrcenol (EINECS 242-362-4)
5-10 wt.-% Verdyl acetate (EINECS 226-501-6)
5-10 wt.-% Cyclamal (EINECS 203-161-7)
5-10 wt.-% 2-tert-Butylcyclohexyl acetate (EINECS 201-828-7)
5-10 wt.-% Amyl salicylate (EINECS 218-080-2)
5-10 wt.-% Ethylene brassilate (EINECS 203-347-8)

Apple-Cinnamon contains the following major components:
25-50% Cinnamaldehyde (EINECS 203-213-9)
5-10% Galaxolide (EINECS 214-946-9)
The EINECS number refers to the European Inventory of Existing Commercial Chemical Substances.

It was surprisingly found that this effect of the destabilizing agent may be prevented by addition of an inert material to the core material of the microcapsules.

"Inert materials" according to the present invention are compounds or compositions that do not react with any of the components of the microcapsule, i.e., the components of the core material, and the components of the microcapsule shell. In particular, the inert material does not destabilize the sheath of the disintegrants. Furthermore, the inert material does not interfere with the microcapsule formation. In addition, the inert material does not react with the active ingredient in the core material. The inert material is completely mixable with the core material of the microcapsules. Accordingly, the inert material has very few or no reactive functional groups and has a low number of double bounds. The inert material can, for example, have no double bonds.

In an embodiment of the present invention, the inert material can, for example, be an organic compound with at least eight C-atoms. Organic compounds with less than eight C-atoms have a high vapor pressure and a high tendency for diffusion. Moreover, smaller molecules provide a risk of causing a fire. It is assumed that the inert material according to the present invention interacts with the surface of the disintegrants and thus protects the disintegrants from the destabilizing agent such as plasticizer and solvents. The chain length of the inert material can, for example, be in the range from 8 to 25 C-atoms, for example, in the range from 10 to 20 C-atoms. Examples of suitable inert materials of the invention are isopropylmyristate (IPM), LINPAR® C14-C20, waxes, polyethylenglycol (PEG) and gasoline fractions with a carbon chain of more than 10 C-atoms, for example, in the range from 14 to 22 C-atoms.

The amount of the inert material in the core of the microcapsules based on the total amount of the core material is at least 5 wt.-%, for example, the concentration is at least 10 wt.-%, for example, at least 20 wt.-%. A concentration below 5 wt.-% may not be enough to protect the disintegrant from the action of the destabilizing agent. The more inert material is added to the core material the less active ingredient can be contained. The maximum concentration of core material is thus dependent on the amount of active ingredient needed for a particular application. In general, the maximum amount of inert material in the core material is at most 50% wt.-%, for example, at most 40 wt.-%, for example, at most 30 wt.-%.

Destabilizing agents such as plasticizers are, for example, found in perfume oils. As shown in Example 8, some disintegrants according to the present invention are destabilized when dispersed in different destabilizing agents. An embodiment of the microcapsule according to the present invention comprises a core material containing a disintegrant, a fragrance oil and an inert material.

In an embodiment of the present invention, the microcapsule can, for example, contain a core comprising an active ingredient, siloxane hydrophobizing agent and an inert material. It was found that the inert material according to the present invention also improves the microcapsule formation in case of in situ hydrophobizing. In particular, the addition of an inert material leads to a higher yield of disintegrant, in particular core/sheath disintegrant in the microcapsule product.

In an embodiment of the present invention, the microcapsule can, for example, contain a shell formed by phloroglucin and glutaraldehyde, and a core comprising a hydrophobized disintegrant consisting of an expandable particle comprising a particle sheath of PMMA and a particle core made of a liquid or gaseous hydrocarbon having a boiling point in the range from 40 to 150° C., and LINPAR® C14-C20.

In an embodiment of the present invention, the microcapsule can, for example, contain a shell formed by phloroglucin and glutaraldehyde, and a core comprising a hydrophobized disintegrant consisting of an expandable particle comprising a particle sheath of polyacrylonitrile and a particle core made of a liquid or gaseous hydrocarbon having a boiling point in the range from 40 to 150° C., and LINPAR® C14-C20.

In an embodiment of the present invention, the microcapsule can, for example, contain a shell formed by phloroglucin and glutaraldehyde, and a core comprising a hydrophobized disintegrant consisting of an expandable particle comprising a particle sheath of PMMA and a particle core made of a liquid or gaseous hydrocarbon having a boiling point in the range from 40 to 150° C., and isopropylmyristate (IPM).

In an embodiment of the present invention, the microcapsule can, for example, contain a shell formed by phloroglucin and glutaraldehyde, and a core comprising a hydrophobized disintegrant consisting of an expandable particle comprising a particle sheath of polyacrylonitrile and a particle core made of a liquid or gaseous hydrocarbon having a boiling point in the range from 40 to 150° C., and isopropylmyristate (IPM).

In an embodiment of the present invention, the microcapsule can, for example, contain a shell formed by phloroglucin and glutaraldehyde, and a core comprising a hydrophobized disintegrant consisting of an expandable particle comprising a particle sheath of PMMA and a particle core made of a liquid or gaseous hydrocarbon having a boiling point in the range from 40 to 150° C., a siloxane hydrophobizing agent and isopropylmyristate (IPM).

In an embodiment of the present invention, the microcapsule can, for example, contain a shell formed by phloroglucin and glutaraldehyde, and a core comprising a hydrophobized disintegrant consisting of an expandable particle comprising a particle sheath of polyacrylonitrile and a particle core made of a liquid or gaseous hydrocarbon having a boiling point in the range from 40 to 150° C., a siloxane hydrophobizing agent and isopropylmyristate (IPM).

In an embodiment of the present invention, the microcapsule can, for example, contain a shell formed by phloroglucin and glutaraldehyde, and a core comprising a hydrophobized disintegrant consisting of an expandable particle comprising a particle sheath of PMMA and a particle core made of a liquid or gaseous hydrocarbon having a boiling point in the range from 40 to 150° C., a siloxane hydrophobizing agent and LINPAR® C14-C20.

In an embodiment of the present invention, the microcapsule can, for example, contain a shell formed by phloroglucin and glutaraldehyde, and a core comprising a hydrophobized disintegrant consisting of an expandable particle comprising a particle sheath of polyacrylonitrile and a particle core made of a liquid or gaseous hydrocarbon having a boiling point in the range from 40 to 150° C., a siloxane hydrophobizing agent and LINPAR® C14-C20.

In an embodiment of the present invention, the microcapsule can, for example, contain a shell formed by phloroglucin and glutaraldehyde, and a core comprising a hydrophobized disintegrant consisting of an expandable particle comprising a particle sheath of PMMA and a particle core made of a liquid or gaseous hydrocarbon having a boiling point in the range from 40 to 150° C., a siloxane hydrophobizing agent selected from Tego® Phobe 1500N, Tego® Phobe 1505, Tego® Phobe 1401 and Tego® Phobe 6010, and isopropylmyristate (IPM).

In an embodiment of the present invention, the microcapsule can, for example, contain a shell formed by phloroglucin and glutaraldehyde, and a core comprising a hydrophobized disintegrant consisting of an expandable particle comprising a particle sheath of polyacrylonitrile and a particle core made of a liquid or gaseous hydrocarbon having a boiling point in the range from 40 to 150° C., a siloxane hydrophobizing agent selected from Tego® Phobe 1500N, Tego® Phobe 1505, Tego® Phobe 1401 and Tego® Phobe 6010, and isopropylmyristate (IPM).

In an embodiment of the present invention, the microcapsule can, for example, contain a shell formed by phloroglucin and glutaraldehyde, and a core comprising a hydrophobized disintegrant consisting of an expandable particle comprising a particle sheath of PMMA and a particle core made of a liquid or gaseous hydrocarbon having a boiling point in the range from 40 to 150° C., a siloxane hydrophobizing agent selected from Tego® Phobe 1500N, Tego® Phobe 1505, Tego® Phobe 1401 and Tego® Phobe 6010, and LINPAR® C14-C20.

In an embodiment of the present invention, the microcapsule can, for example, contain a shell formed by phloroglucin and glutaraldehyde, and a core comprising a hydrophobized disintegrant consisting of an expandable particle comprising a particle sheath of polyacrylonitrile and a particle core made of a liquid or gaseous hydrocarbon having a boiling point in the range from 40 to 150° C., a siloxane hydrophobizing agent selected from Tego® Phobe 1500N, Tego® Phobe 1505, Tego® Phobe 1401 and Tego® Phobe 6010, and LINPAR® C14-C20.

In an embodiment of the present invention, the microcapsule can, for example, contain a shell formed by phloroglucin and glutaraldehyde, and a core comprising a hydrophobized disintegrant consisting of an expandable particle comprising a particle sheath of PMMA and a particle core made of a liquid or gaseous hydrocarbon having a boiling point in the range from 40 to 150° C., Tego® Phobe 1505, and isopropylmyristate (IPM).

In an embodiment of the present invention, the microcapsule can, for example, contain a shell formed by phloroglucin and glutaraldehyde, and a core comprising a hydrophobized disintegrant consisting of an expandable particle comprising a particle sheath of polyacrylonitrile and a particle core made of a liquid or gaseous hydrocarbon having a boiling point in the range from 40 to 150° C., Tego® Phobe 1505, and isopropylmyristate (IPM).

In an embodiment of the present invention, the microcapsule can, for example, contain a shell formed by phloroglucin and glutaraldehyde, and a core comprising a hydrophobized disintegrant consisting of an expandable particle comprising a particle sheath of PMMA and a particle core made of a liquid or gaseous hydrocarbon having a boiling point in the range from 40 to 150° C., Tego® Phobe 1505, and LINPAR® C14-C20.

In an embodiment of the present invention, the microcapsule can, for example, contain a shell formed by phloroglucin and glutaraldehyde, and a core comprising a hydrophobized disintegrant consisting of an expandable particle comprising a particle sheath of Polyacrylnitrile and a particle core made of a liquid or gaseous hydrocarbon having a boiling point in the range from 40 to 150° C., Tego® Phobe 1505, and LINPAR® C14-C20.

This is of considerable importance in the chemical industry. For instance, in the production of polyurethane, for example, and also in the production of PU foams, catalysts are currently added which already at room temperature develop a considerable activity. This affects the production, since the viscosity of the reaction mixtures greatly increases in the reactors or impregnating tanks used. A catalyst which first becomes active in a desired temperature range, or, for example, is first released during the drying of materials produced in this manner, is, however, not yet known and highly desirable. By using the surface-modified disintegrants according to the present invention, and by using the microcapsules according to the present invention, such catalysts are provided directly. Therefore, in the production of polymer systems using initiators encapsulated in the microcapsules according to the present invention, novel process profiles and property profiles of the products can be obtained which permit the use of initiators, catalysts, mediators, blocking agents, chain-termination reagents, sensitizers, etc. Said contents are first released at a previously defined and do not affect the reactions before the thermally initiated release according to the invention.

The catalysts which can be used and/or encapsulated advantageously in the microcapsules according to the present invention are generally known to those skilled in the art. Organometallic compounds can, for example, be encapsulated. These are organometallic compounds of the main group and subgroup elements having one or more metal cores such as, for example, triethylaluminium, organostannanes and the like. Ziegler-Natta catalysts or metallocenes can also be encapsulated using the methods according to the present invention. Further organometallic catalysts are known to those skilled in the art and can be used in the present invention.

In an embodiment, the present invention provides a microcapsule comprising a surface-modified disintegrant as defined above, an organometallic catalyst, for example, triethylaluminium, organostannanes, Ziegler-Natta catalysts or metallocenes, and also a shell material as defined above.

In addition, the present invention relates to products which contain microcapsules or microcapsule dispersions according to the present invention, and use thereof, for example, in a field of application which is selected from the fields of coatings, such as carbon-free self-copy systems, coating and impregnation of papers and security feature coating, catalyst-filled microcapsules, paint technology such as paint production, construction chemistry, dental technology, for example, as a component of rapidly curing dental fillings, self-repairing systems, cosmetics, for example, for fragrance oils and aroma oils, pharmacy, for example, as active ingredient carriers, medical technology, e.g., for encapsulation of emitters of neurotransmitters, such as NO, e.g. of nitroglycerol, washing, cleaning, disinfecting, gluing, flame retardancy, treatment of plants, preferably as fungicide, pesticide, insecticide, herbicide or corrosion protection.

The microcapsules according to the present invention may be used, e.g., for producing paints, e.g., for fragrance paints, and are usable with variations in the degree of crosslinking thereof, the size thereof, the wall thickness thereof, and surface finishing, and also in the core material.

On account of the high chemical and physical resistance, they are suitable as stable core/shell capsule systems, but also for use in aggressive media. For instance, it is possible to produce fragrance paints which are to be coated via conventional spreader systems with the layer thicknesses known in the printing industry, without a significant fraction of the capsules being destroyed.

The microcapsules generally have a median diameter of 1-1000 µm. In the context of the present invention, however, the expression microcapsule also comprises nanocapsules, i.e., capsules having a median diameter <1 μm. The capsules can, for example, have a median diameter from 0.1 to 100 μm. The wall thickness is variable and can be 0.01-100 μm, for example, 0.1 to 10 μm.

The microcapsules according to the present invention can, for example, be used in the form of aqueous dispersions as impregnating resins in the wood/material sector, and are suitable as impregnating resins having additional functions such as catalytic effects, color effects, thermochromic effects or security effects for decorative coating systems.

The present invention further relates to the use of the microcapsules according to the present invention for releasing fragrances in the textile industry, for releasing fragrances and/or hair care and/or skin care products in cosmetics, for releasing catalysts in polymer synthesis or chemical synthesis, and for releasing lubricants in the car and mechanical engineering industry.

FIGS. 1 to 3 show by way of example the thermal opening of microcapsules according to the present invention having a melamine-formaldehyde shell. Micrographs of a dispersion of the microcapsules in a transparent colorless oil at various temperatures are shown in order to clarify the opening of the microcapsules in a defined temperature range. FIG. 1 shows an image at 25° C. The spherical dark microcapsules may be clearly seen still undamaged against the light background. FIG. 2 shows an image at 75° C. The majority of the microcapsules are still undamaged. The start of opening of some microcapsules may readily be seen on the basis of the light circular regions in the dispersion. FIG. 3 shows an image at 85° C. The opening of a multiplicity of the microcapsules may now be seen more clearly than in the image shown in FIG. 2 at 75° C.

FIG. 4 shows an apparatus for investigating the opening temperature range of microcapsules having disintegrants as described in Example 4. In FIG. 4:

Reference number 1: means thermosensor;

Reference number 2: means test tube with filling (test material);

Reference number 3: means glass beaker with thermal oil;

Reference number 4: means magnetic stirrer bar; and

Reference number 5: means heating plate with magnetic stirrer.

FIG. 5 shows a drawing of a device for measuring the electrophoretic mobility (EM) as a measure of the zeta potential. FIG. 5 *a*) shows a side view where reference number 6 means glass capillary and reference number 7 means platinum electrodes. FIG. 5 *b*) shows a plan view where reference number 7 means platinum electrodes.

FIG. 6 shows the results of an encapsulation of core/sheath disintegrants into microcapsules. The encapsulated core material contains a siloxane in FIG. 6 *a*). The encapsulated core material does not contain comprised a hydrophobizing agent in FIG. 6 *b*).

The present invention will hereafter be clarified by various examples. In this case, the examples are in no way limiting for the claimed subject matter of the present invention, but only serve to illustrate the invention to a person skilled in the art.

Example 1—Production of a Surface-Modified Disintegrant

A 10% strength aqueous solution of benzalkonium chloride was produced from benzalkonium chloride and demineralized water. As disintegrant, 600 g of Expancel® 461DU (from AkzoNobel) were suspended in 400 g of demineralized water (ratio of Expancel®:water 1:1) at a stirrer speed of 2500 rpm over 5 min, and then admixed with the aqueous benzalkonium chloride solution with stirring, in such a manner that the weight fraction of the benzalkonium chloride was 1.5% of the weight of the Expancel®. The aqueous dispersion obtained in this manner was filtered by suction, washed twice with 300 g of demineralized water, and the resultant filter cake was dried at 45° C. for 24 hours on filter paper. Then the filter cake was able to be comminuted into the surface-modified Expancel® microspheres. The resultant surface-modified disintegrants were able to be distributed directly homogeneously in oil (ND 100 slip agent). Demineralized water was added to the oil/disintegrant dispersion and, after shaking several times, the phase in which the surface-modified disintegrant concentrated was examined. It was found that the surface-modified, e.g., Expancel® microspheres may be found in the oil phase, but not in the aqueous phase. Disintegrants were obtained thereby, the surface of which had been hydrophobized.

Comparative Example 1—Disintegrant Without Surface Modification

Expancel® 461 DU (from AkzoNobel) was added to oil (ND 100) and then demineralized water was added. After shaking several times, the phase in which the Expancel® microspheres concentrated was examined. It was found that the microspheres were found throughout both phases, which is disadvantageous for encapsulation together with a hydrophobic active ingredient (for instance an oil).

Example 2—Disintegrant with Surface Modification

The surface-modified Expancel® 461 DU disintegrants were incorporated at 10% in C14-C17 Paraffin (LINPAR® C14-17 from Sasol) and approximately 5 ml of this mixture were charged into a thin-wall test tube. This test tube was positioned centrally in a glass beaker filled with PEG 400 as oil bath on a magnetic heating plate controlled by a thermosensor. The meniscus of the disintegrant-paraffin dispersion was adjusted to the height of the meniscus of the oil bath and this was circulated with a magnetic stirrer at a heating rate of approximately 2° C./min, in order to ensure uniform temperature distribution and a uniform heating rate. The heating rate was approximately 2° C./min in the expected expansion range of the surface-modified Expancel® particles.

The expansion started at 94° C. and achieved its maximum at 96° C. These values correspond to untreated Expancel® 461 DU particles. Therefore, the surface treatment according to the present invention has no effect on the expansion temperature.

Production of stable core/shell microcapsules with active ingredient and surface-modified disintegrants:

Example 3—Phloroglucinol-Melamine Microcapsule a) Production of the Precondensate 5.4 g of phloroglucinol and 0.6 g of melamine are dispersed in 78.6 g of distilled water. The pH is adjusted to 3 using 1.2 g of 85% strength formic acid. The mixture is heated to 35° C. and 14.2 g of 50% strength glutaraldehyde solution are added. After 5 min, the soluble precondensate begins to form, recognizable from the fact that the sparingly water-soluble phloroglucinol and melamine dissolves. The total solids of the precondensate is 14.0% by weight.

b) Production of the Microcapsule 41.5 g of the soluble precondensate obtained in stage a) are admixed after 5 min with 3.0 g of the protective colloid, a copolymer of AMPS (2-acrylamido-2-methyl-1-propylsulphonic acid) and PEM 6 (polyethylene glycol monomethacrylate) and 23.7 g of a fragrance oil that is to be encapsulated (Radiance) and the disintegrant obtained according to Example 1 (ratio fragrance oil:disintegrant=70:30). For particle formation, at the same time, the speed of rotation is increased from 500 rpm to 2500 rpm. After 20 min, the resin starts to cure to form structured capsule walls. In the following hour stirring is performed at a speed of rotation of 600 rpm. In the course of this hour, after 15 min, 7.5 g of a 14% strength by weight phloroglucinol slurry acidified to pH 3 with formic acid (85%) is added for 45 min, and after 20 min, 16 g of water are added, in order to prevent thickening of the slurry. Thereupon, a 2-hour curing phase at 80° C. follows. Then, 4.2 g of a 33% strength by weight melamine slurry (Folco slurry) acidified with formic acid 85% is added for ½ h. Finally, post-curing is performed for ½ h at pH 3. The capsule slurry is cooled to room temperature and adjusted to pH 7 using sodium hydroxide solution. Technical data of the resultant microcapsule:

Diameter D(90): 10 µm
Solids: 33%
Core fraction: 70%
Efficiency: 90%
Powder yield: 90%
Residual aldehyde content: <500 ppm, determined by GC (FT-IR)

A sample of the microcapsules thus obtained was dispersed in colorless oil and examined by means of a microscope as to whether Expancel® particles were still to be found outside the microcapsules according to the invention. It was found that no Expancel® particles were visible outside the microcapsules according to the invention. Therefore, it was able to be shown that the production of microcapsules from a hydrophobic oil, the surface-modified disintegrants according to the invention, and the base materials for the capsule sheath was successful according to the present invention.

Example 4—Examination of the Thermal Opening of the Microcapsules

Figure 2:
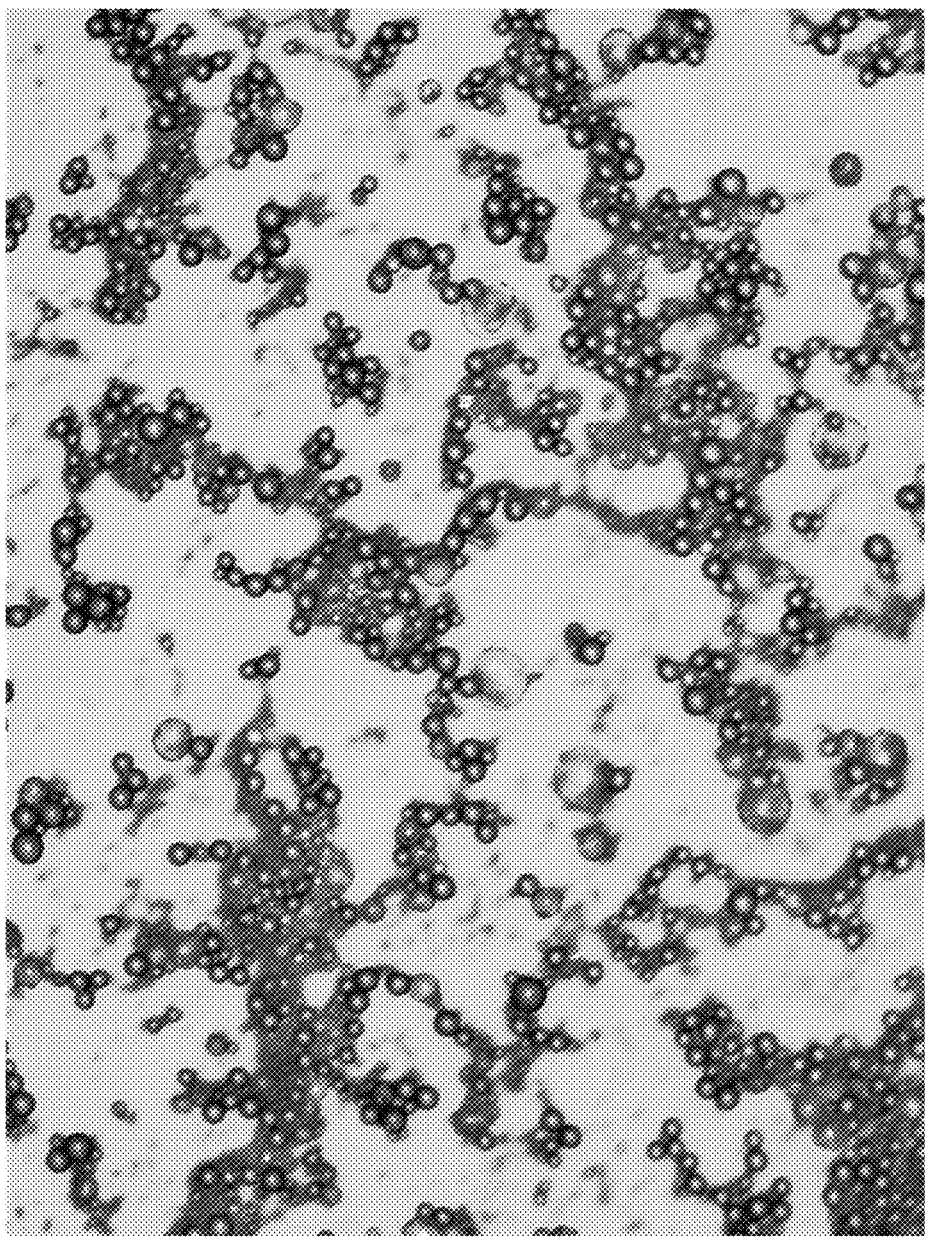
FIG. 2 shows the thermal opening of microcapsules according to the present invention having a melamine-formaldehyde shell.
Figure 3:
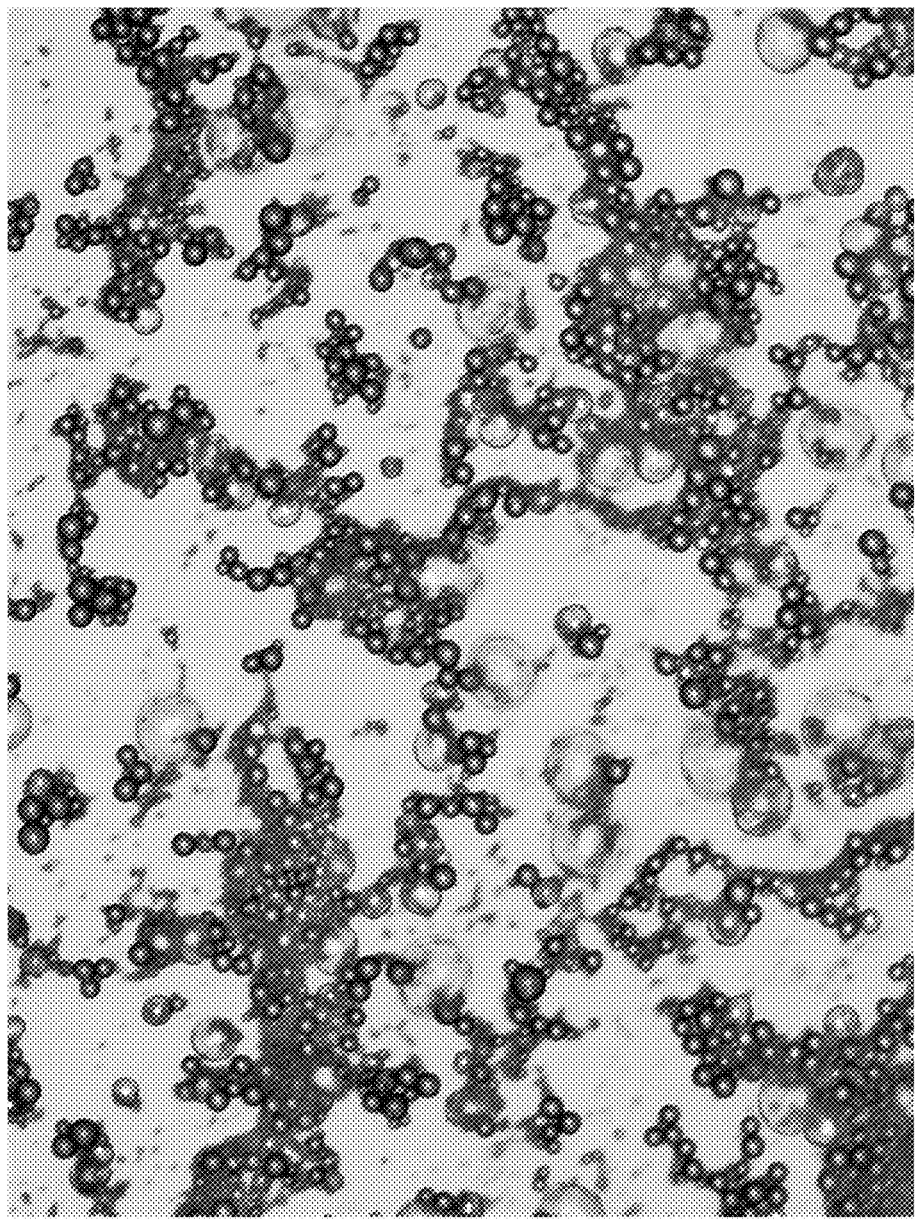
FIG. 3 shows the thermal opening of microcapsules according to the present invention having a melamine-formaldehyde shell.
Figure 4:
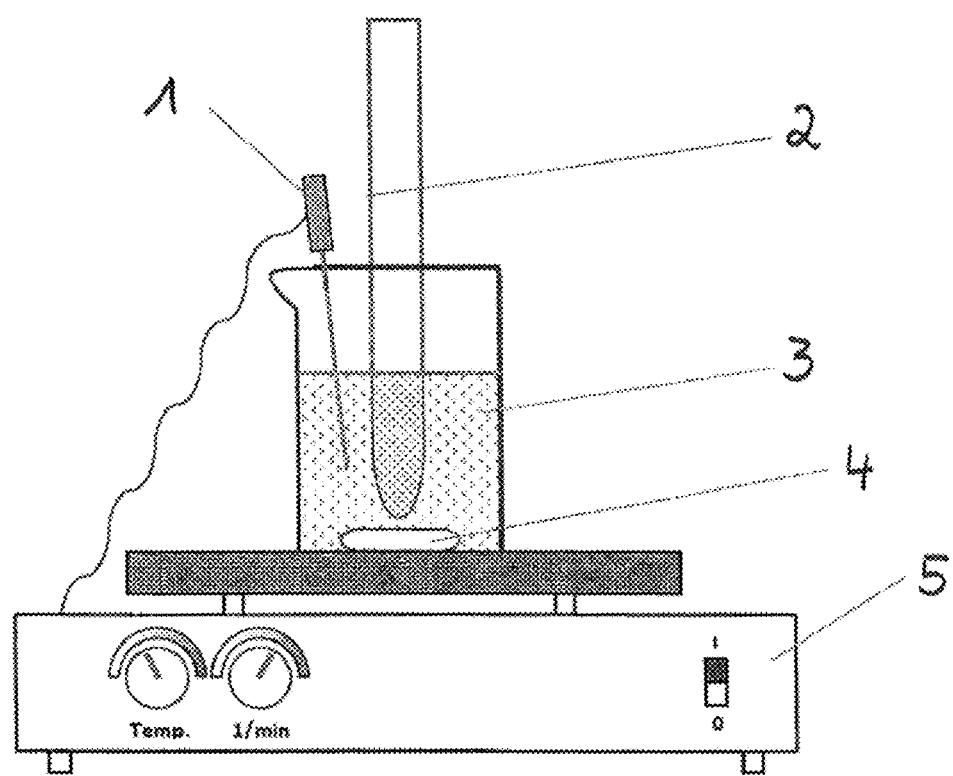
FIG. 4 shows a drawing of an apparatus for investigating the opening temperature range of microcapsules having disintegrants as described in Example 4.
Figure 5:
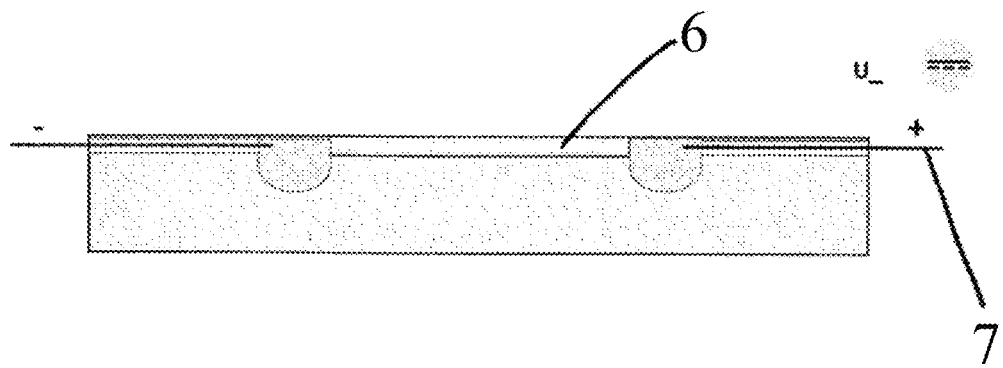
FIG. 5 shows a drawing of a device for measuring the electrophoretic mobility (EM) as a measure of the zeta potential.
Figure 5:
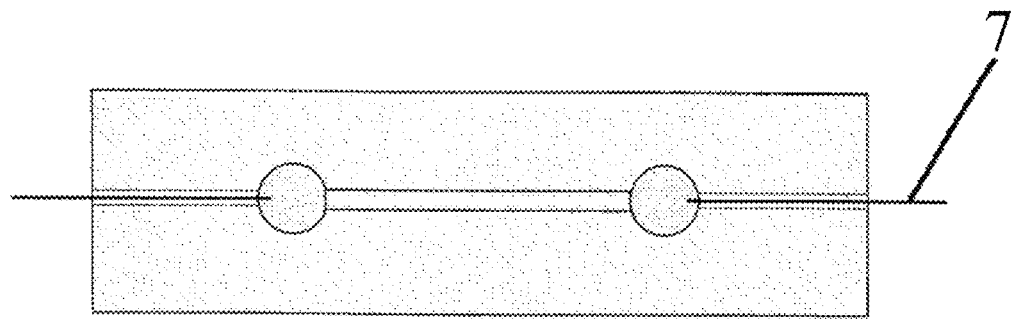

The oil dispersion of the microcapsules according to the invention obtained in Example 3 was placed in a test tube in an apparatus as shown in FIG. 4 and a heating rate of approximately 2° C./min was generated by means of the heating plate. Via a microscope, the opening of the microcapsules was then examined at various temperatures. As expected, at room temperature, there was still no opening, and not until increasing temperatures in the opening region predetermined by the expansion temperature could the opening of the microcapsules according to the invention as shown in FIGS. 1 to 3 be observed.

Example 5—Use Example A

The microcapsules obtained in Example 3 were transferred to a paint and applied to a paper surface. In this manner, a surface was generated which releases a fragrance on the action of a defined temperature. The microcapsules according to the present invention are therefore, for example, outstandingly suitable for applications in the advertising, cosmetics, body care and perfume industry.

Example 6—Use Example B

Similarly to the procedure of Example 3, dimethyltin neodecanoate (Fomrez tin catalyst UL-28, obtained from Momentive performance materials) was encapsulated with 30% Expancel® DU 40 as disintegrant, which had been surface-modified with 0.5% Lupasol PS, firstly in melamineformaldehyde microcapsules, and secondly in phloroglucinol-glutaraldehyde capsules.

The capsules were examined as in Example 3 for the encapsulation thereof, and as in Example 4 for the thermal opening thereof. Not only in the formaldehyde-melamine microcapsules, but also in the phloroglucinol-glutaraldehyde microcapsules, an encapsulation of the catalyst and of the disintegrant was observed. Both microcapsule systems opened at the expected temperature and released the catalyst.

An encapsulated catalyst for polyurethane synthesis (PU synthesis) was thereby provided which is first released in a narrow and exactly definable temperature range. This is advantageous in the planning of the production of PU and/or PU products such as coatings, foams and the like. As a result, likewise, the excellent suitability of the microcapsules of the present invention for the targeted release of catalysts and other substances in chemical synthesis and in chemical industry methods is made clear.

Example 7—Determination of Electrophoretic Mobility

To determine the electrophoretic mobility and the zeta potential that can be calculated therefrom, various measurement cells were constructed in order to enable determination under what conditions reproducible results may be determined. The basis for the method described is that particles migrate to the corresponding electrode at a defined velocity in an electric field according to the surface charge thereof (positively charged particles to the negatively charged electrode). This basic principle is used, e.g., in electrophoresis, and for some time also for the zeta potential measurement. The purpose of the experiments should be to develop a measurement method suitable for the range of application (microcapsules/microspheres in the particle size range from >5 µm to <40 µm), with which comparative measurements become possible (e.g., recognition of trends with respect to cationization).

For the measurement, the test material is mixed with a suitable liquid and charged into one of the two recesses in the measurement cell. On account of capillary action, the tube becomes completely flooded. If this is taking place, the second chamber is charged. As a result of the hydrostatic paradox (communicating tubes), an equal liquid level is established between the chambers. This procedure takes approximately 1 to 10 min in the configuration described, according to viscosity of the diluent used. The complete level equalization is recognizable by observing the capillary with the microscope. When the particles no longer flow in any direction, the actual measurement can be begun.

For this purpose, the electrodes are connected to the voltage source (direct current circuit part 5-24 V). On the microscope, a suitable focal plane is established over the capillary (100-fold enlargement), in such a manner that the capsules are pictured with reasonable sharpness. In the microscope software, a suitable time sequence (serial recording) is set. Thereafter, the voltage source is switched on and the sequential recording is started after approximately 1 minute.

After the recording, the time sequence can be played back, capsules selected via consideration of individual pictures can be observed in migration thereof, and the path covered can be measured. From the path covered, the speed is calculated (cm/s). In addition, the direction of migration (anode or cathode) is determined.

The zeta potential may be calculated, according to the present application, i.e., according to the following formula:

$$\zeta = \frac{4\pi\eta}{\varepsilon} \times U \times 300 \times 300 \times 1000$$

$\zeta$ = Zeta Potential (mV)

$\eta$ = Viscosity of Solution $E$ = Dielectric Constant $U = \frac{v}{V/L}$: Electrophoretic Mobility $v$ = Speed of Particle (cm/sec)

$V$ = Voltage (V)

$L$ = The distance of Electrode

Further formulae:

$$v = \mu e * E$$

(v=migration speed [cm/s]; µe=electrophoretic mobility; E=electric field strength [V/m])

$$E = U/d$$

(electric field strength [V/m]=voltage [V]/electro

Example 8—Stability of the Disintegrants

The stability of different core/sheath disintegrants in fragrance oils Detergaflor II and Fougere Cap was tested. The following core/sheath disintegrants were used:

TABLE 4

Characteristics of the Tested Core/Sheath Disintegrants

| | Disintegrant | | |
|---|---|---|---|
| | Matsumoto ® F 36 | Expancel ® 031WUF40 | Expancel ® 007WUF40 |
| Diameter D(50) [µm] | 10-16 | 10-16 | 10-16 |
| Expansion Temperature $T_{start}$ [° C.] | 70-80 | 80-95 | 91-99 |
| Expansion Temperature $T_{max}$ [° C.] | 110-120 | 120-135 | 138-143 |
| Solvent Resistance | Low | Low | Low |

The test was performed using the following method:

The disintegrants were mixed in the fragrance oil and added to a microscope slide. The microscope slide was placed onto a heating plate and heated to 110° C. The disintegrants were observed during heating under the microscope. Table 5 summarizes the results observed for the disintegrants in Detergaflor II.

TABLE 5

Results of Incubation of Disintegrants in Detergaflor II

| | Detergaflor II | |
|---|---|---|
| Disintegrant | Observed Expansion Temperature (° C.) | Observations |
| Matsumoto ® F36 | 77 | A reduced expansion of the disintegrant was followed by rapid contraction |
| Expancel ® 031WUF40 | 77 | A reduced expansion of the disintegrant was followed by rapid contraction |
| Expancel ® 007WUF40 | 81 | A part of the disintegrants shrinked rapidly after expansion. The other part showed a higher thermal stability and expanded further until reaching 110° C. |

The results of the incubation of the disintegrants in the fragrance oil Fougere Cap are summarized in Table 6:

TABLE 6

Results of Incubation of Disintegrants in Fougere Cap

| | Fougere Cap | |
|---|---|---|
| Disintegrant | Observed expansion temperature (° C.) | Observations |
| Matsumoto ® F36 | 75 | A reduced expansion of the disintegrant was followed by very rapid contraction |
| Expancel ® 031WUF40 | 73 | A reduced expansion of the disintegrant was followed by rapid contraction |
| Expancel ® 007WUF40 | 73 (91) | A part of the disintegrants shrinked rapidly after expansion. The other part expanded at 91° C. and then also shrinked rapidly. |

The experiment shows that in the tested fragrance oils the stability of the core/sheath disintegrant was drastically reduced.

Example 9—Effect of Inert Materials on Stability of the Disintegrants

The experiment described in example 8 was repeated with the addition of the inert materials according to the invention (LINPAR® C14-C17 and Isopropylmyristate) into the fragrance oils.

The following Table 7 summarizes the observations after incubation of the disintegrants in solution of 80 wt.-% of the fragrance oil Detergaflor II and 20 wt.-% LINPAR® C14-C17:

TABLE 7

Results of the experiment with Detergaflor II and LINPAR ® C14-C17

| | Detergaflor II and 20 wt.-% of LINPAR ® C14-C17 | |
|---|---|---|
| Disintegrant | Observed expansion temperature (° C.) | Observations |
| Matsumoto ® F36 | 80 | Good expansion. Slow shrinkage. At 110° C. the disintegrants were not expanded anymore. |

TABLE 7-continued

Results of the experiment with Detergaflor
II and LINPAR ® C14-C17

| Disintegrant | Detergaflor II and 20 wt.-% of LINPAR ® C14-C17 | |
|---|---|---|
| | Observed expansion temperature (° C.) | Observations |
| Expancel ® 031WUF40 | 79 | Good expansion. Slower shrinkage as compared to F36. At 110° C. there was still a slow shrinkage. |
| Expancel ® 007WUF40 | 85 | Good expansion. No shrinkage at 110° C. |

Table 8 summarizes the observations after incubation of the disintegrants in solution of 80 wt.-% of the fragrance oil Detergaflor II and 20 wt.-% isopropylmyristate.

TABLE 8

Results of the experiment with Detergaflor
II and isopropylmyristate

| Disintegrant | Detergaflor II with 20 wt.-% of Isopropylmyristate | |
|---|---|---|
| | Observed expansion temperature (° C.) | Observations |
| Matsumoto ® F36 | 79 | Good expansion. Slow shrinkage. At 110° C. the disintegrants were not expanded anymore. |
| Expancel ® 031WUF40 | 77 | Good expansion. Slower shrinkage as compared to F36. At 110° C. there was still a slow shrinkage. |
| Expancel ® 007WUF40 | 86 | Good expansion. No shrinkage at 110° C. |

Table 9 displays the results of the incubation of the disintegrants in solution of 80 wt.-% the fragrance oil Fougere Cap and 20 wt.-% of LINPAR® C14-C17.

TABLE 9

Results of the experiment with Fougere
Cap and LINPAR ® C14-C17.

| Disintegrant | Fougere Cap and 20 wt-% of LINPAR ® C14-C17 | |
|---|---|---|
| | Observed expansion temperature (° C.) | Observations |
| Matsumoto ® F36 | 82 | Good expansion. Very slow shrinkage after expansion. At 110° C. the disintegrants were not expanded anymore. |
| Expancel ® 031WUF40 | 80 | Good expansion. Slower shrinkage as compared to F36. At 110° C. there was still a slow shrinkage. |
| Expancel ® 007WUF40 | 86 | Good expansion. No shrinkage at 110° C. |

The following Table 10 displays the results of the incubation of the disintegrants in solution of 80 wt.-% the fragrance oil Fougere Cap and 20 wt.-% of isopropylmyristat.

TABLE 10

Results of the experiment with Fougere
Cap and LINPAR ® C14-C17

| Disintegrant | Fougere Cap and 20 wt.-% of Isopropylmyristat | |
|---|---|---|
| | Observed expansion temperature (° C.) | Observations |
| Matsumoto ® F36 | 81 | Good expansion. Slow shrinkage. At 110° C. the disintegrants were not expanded anymore. |
| Expancel ® 031WUF40 | 79 | Good expansion. Slower shrinkage as compared to F36. At 110° C. there was still a slow shrinkage. |
| Expancel ® 007WUF40 | 90 | Good expansion. No shrinkage at 110° C. |

The experiment shows that the functionality of a disintegrant in a core material containing a destabilizing agent core material can be maintained by addition of an inert material such as IPM or LINPAR® C14-C20.

Example 10—Production of Microcapsules with Phloroglucin-Glutaraldehyde Shell and Hydrophobized Disintegrants Step 1—Hydrophobic Coating of the Core/Sheath Disintegrants Alternative A—Disintegrant Expancel® 920 WUF40 and Hydrophobizing Agent Disperbyk® 180

In a beaker 5 g Disperbyk® 180 were added to 500 g toluene and the mixture was homogenized by stirring. 100 g core/sheath disintegrant Expancel® 920 WUF40 was dried in a recirculating air drying oven at a temperature of 45° C. until reaching a constant weight. The disintegrants were mixed with the Disperbyk® 180/toluene—mixture by means of a dissolver for 15 min at a stirring speed of 500 rpm. The homogenized suspension was added to a crystallization dish and the toluene was evaporated first at room temperature and afterwards at 45° C. in the recirculating air drying oven. The dried disintegrants were applied to a sieve to exclude disintegrants with a size of less than 500 µm.

Alternative B—Disintegrant Expancel® 007 WUF40, Hydrophobizing Agent Tego® Phobe R1401

141 g disintegrant (Expancel® 007 WUF40) corresponding to a dry mass of 100 g were added to 500 g VE-water under tearing in a dissolver at a speed of 500 rpm. While stirring 9.1 g Tego® Phobe R141 (corresponding to 5 g solvent free hydrophobizing agent) were added to the Expancel®/water dispersion. After 30 min of stirring the disintegrants were separated from the dispersion by means of filtering. The filter cake was added to the crystallization dish and dried in an air recirculation drying oven of a temperature of 45° C. The dried disintegrants were applied to a sieve to exclude disintegrants with a size of less than 500 µm.

Step 2—Formation of the Core Material

Alternative A

For formation of the core material 20 g dried Expancel® 920 WUF40 were added to 18 g of the liquid thin catalyst FOM-REZ® UL 38 and stirred in a dissolver at the speed of 4400 rpm for about 15 min. The homogenized dispersion was then directly used for microcapsule formation as described in step 3.

Alternative B

For the formation of the core material 40 g Expancel® 007 WUF40 were added to 160 g FOM-REZ® UL 38 and stirred in a dissolver at a speed of 4,400 rpm for 15 min. The homogenized dispersion was then used for the formation of microcapsules as described in step 3.

Step 3—Encapsulation

In a 400 ml beaker, 5.5 g resorcinol were dissolved in 70 g mater under stirring (stirring speed about 1,500 rpm) and thereafter 2.0 g sodium carbonate solution added (20 wt.-%), resulting in a pH-value about 7.9. This solution was warmed to a temperature of about 52° C. Then, 25.5 g glutaraldehyde were added.

The mixture was stirred for about another 10 min at a speed of about 1,500 rpm and at a temperature of about 52° C. (pre-condensation). Thereafter, about 20 g water were added and about 2 min later 1 g of one of a protective colloid a) copolymer 1a, b) copolymer 1b and c) poly AMPS (AMPS-homopolymer); and again about 2 min later 55 g Palatinol A (=diethylphtalate) added. Directly following, the stirring speed was increased to about 4,000 rpm and at about the same time 20.0 g of sodium carbonate solution (20% by weight) added. Afterwards, the pH-value of the mixture was about 9.7. Thereafter, the viscosity and the volume of the mixture increase. Stirring continues at a stirring speed of about 4,000 rpm, until the viscosity was decreasing. Only then, the stirring speed was lowered to about 1,500 rpm. At a temperature of about 52° C., the batch was being stirred for about another 60 min at a speed of 1,500 rpm. This phase was the resting phase. In the following, the mixture was heated to about 80° C. and the capsules hardened at this temperature over a period of 3 hours.

Capsule size distribution—D (90) 5-10 µm: capsulation efficiency about 9%: Drying yield was >90%; solid body of the slurry was about 40% by weight.

The so-produced capsules were free of formaldehyde and can be further processed as stable core/shell—microcapsules from the aqueous slurry into a dry free-flowing powder.

Example 11—Production of Thermally Opening Microcapsules with In Situ Hydrophobic Treatment Step 1—Preparation of the Core Material/in situ Hydrophobic Treatment 50 g disintegrant (Expancel 920 WUF40) was dried in a drying oven at 45° C. until reaching a constant weight 229.9 g fragrance oil (Deterga Flor II), 25.6 g of solvent adjuvant (LINPAR® C14-C17) and 11.4 g of a siloxane hydrophobizing agent (Tego® Phobe 1505) were mixed in a beaker while stirring at 600 rpm. 28.3 g dried disintegrant (Expancel® 920 WUF40) were added. Consequently, the stirring speed was increased to 3,500 rpm and the mixture was further dispersed for 10 min.

Step 2—Preparation of the Precondensate Solution and Encapsulation of the Core Material 57 g of an ethylene imine polymer with high cationic charge (Lupasol® PS) and 18.72 g of melamine precondensate (Luracoll® SD) were solved in 346.8 g water and heated to a temperature of 40° C. while stirring at 600 rpm. At this stage the pH was set to 3.5 and the reaction of the components was allowed for 20 min. After 10 min of reaction the pH was reset to 3.5.

The core material obtained in step 1 was added to the precondensate at a stirring speed of 1000 rpm and after 1 minute the stirring speed was increased to 1,500 to 2,000 rpm. When the particle size of D90=50-60 µm, D50=30-40 µm was reached the stirring speed was reduced to 1100 rpm. This was followed by the standard procedure: one hour resting at 40° C., two hours hardening at 80° C. with 30% of the theoretical amount of a melamine-formaldehyde prepolymer with $H_2O_2$.

Figure 6:
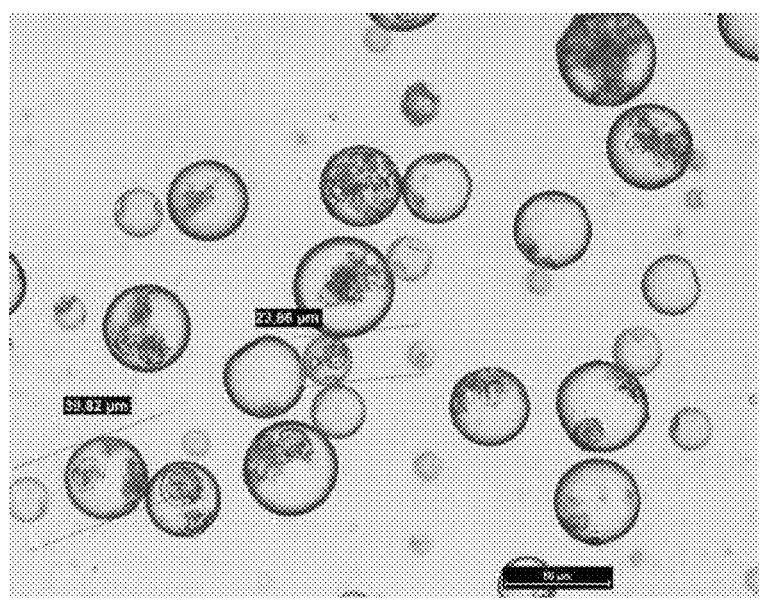
FIG. 6 shows the results of an encapsulation of core/sheath disintegrants into microcapsules.
Figure 6:
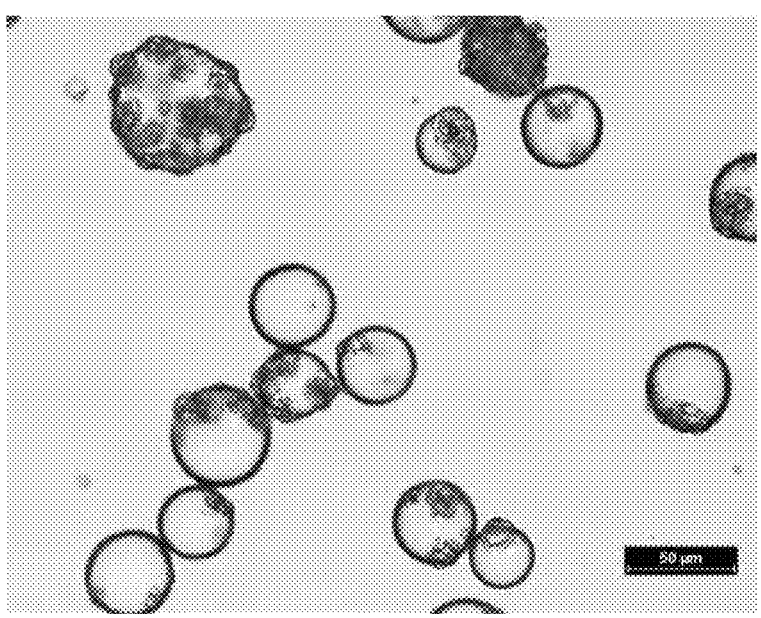

The same experiment was carried out without the addition of the hydrophobizing agent. In FIG. 6 a) and b), the results of the two experiments with and without siloxane hydrophobizing agent was shown.

In FIG. 6 a), most of the disintegrants (small spheres) were located inside the microcapsules (large spheres). In contrast, without using Siloxane hydrophobizing agent the disintegrants were located on the surface of the microcapsules but not inside the microcapsules (FIG. 6 b)).

Example 12—Practical Application of Microcapsules Comprising Disintegrants and Perfume Oil In this experiment the microcapsules were tested in the washing, drying and ironing of clothes.

Accordingly, in test 1 in two washing machines 5 pieces of cloth were washed at once for 40 min at a maximum temperature of 60° C. (program "easy-care") with no laundry agent but 20 g of fabric conditioner including a slurry of microcapsules (concentration 1%). The microcapsules in the tests contained the perfume oils Detergaflor or Fougere Cap and either 10% of Expancel® 920 WUF 40% as disintegrant or no disintegrant.

In the same set up the test was repeated with slurries with different concentrations of microcapsules (2% and 4%) were carried out.

After washing the pieces of cloth were dried in a tumble drier with the program "cupboard dry" at a temperature of 80° C. The dried pieces of cloth were then ironed at a temperature of 140° to 150° C. (program "cotton").

Directly after washing, after drying, after ironing and 24 h after ironing the pieces of cloth were tested for the intensity of the emitted fragrance.

The results were summarized in Table 11. The fragrance values 1 to 4 in the Table 9 represent the following the following test results.
1: No fragrance
2: Low fragrance
3: Fragrance easily sensed
4: Intensive Fragrance

TABLE 11

Fragrance values of pieces of cloth after the individual steps washing, drying and ironing.

| | | | Washing Machine | | After Washing all cloth | After Dry tumbler | | | | | 1 min after ironing | | | | | 24 h after ironing | | | | |
|---|---|---|---|---|---|---|---|---|---|---|---|---|---|---|---|---|---|---|---|---|
| Test | Disintegrant | Agent | Microcapsule in Slurry [%] | Amount of Agent [g] | | C1 | C2 | C3 | C4 | C5 | C1 | C2 | C3 | C4 | C5 | C1 | C2 | C3 | C4 | C5 |
| 1 | None | Conditioner | 1 | 20 | 3 | 1 | 1 | 1 | 1 | 1 | 1 | 1 | 1 | 1 | 1 | 1 | 1 | 1 | 1 | 1 |
|   | 10% Expancel ® 290WUF40 | Conditioner | 1 | 20 | 3 | 1 | 1 | 1 | 1 | 1 | 1 | 2 | 1 | 1 | 1 | 1 | 1 | 1 | 1 | 1 |
| 2 | None | Conditioner | 2 | 20 | 3 | 1 | 1 | 1 | 1 | 1 | 1 | 1 | 1 | 1 | 1 | 1 | 1 | 1 | 1 | 1 |
|   | 10% Expancel ® 290WUF40 | Conditioner | 2 | 20 | 3 | 1 | 1 | 1 | 1 | 1 | 2 | 2 | 2 | 1 | 2 | 2 | 2 | 2 | 1 | 2 |
| 3 | None | Conditioner | 4 | 20 | 3 | 1 | 1 | 1 | 1 | 1 | 1 | 1 | 1 | 1 | 1 | 1 | 1 | 1 | 1 | 1 |
|   | 10% Expancel ® 290WUF40 | Conditioner | 4 | 20 | 3 | 1 | 1 | 1 | 1 | 1 | 3 | 3 | 3 | 3 | 3 | 3 | 3 | 3 | 3 | 3 |

What is claimed is:

1. A microcapsule comprising:
a shell; and
a core comprising at least one active ingredient and at least one surface-modified disintegrant,
wherein, the at least one surface-modified disintegrant is an expandable particle comprising a particle core and a particle sheath.

2. The microcapsule as recited in claim 1, wherein a surface of the at least one surface-modified disintegrant is hydrophobized.

3. The microcapsule as recited in claim 1, wherein the microcapsule opens at a temperature of below 150° C.

4. The microcapsule as recited in claim 2, wherein the surface of the at least one surface-modified disintegrant is hydrophobized with a compound selected from the group consisting of a polyethylene imide, a quaternary ammonium compound, a quaternary polyvinyl pyrrolidone, and oleic acid.

5. The microcapsule as recited in claim 2, wherein the surface of the at least one surface-modified disintegrant is hydrophobized with a compound selected from the group consisting of benzalkonium chloride and didecyldimethylammonium chloride.

6. The microcapsule as recited in claim 1, wherein the shell comprises a wall material selected from the group consisting of melamine-formaldehyde, phloroglucinol-melamine, phloroglucinol-glutaraldehyde, resorcinol-glutaraldehyde, melamine-glutaraldehyde, and melamine-urea-formaldehyde.

7. The microcapsule as recited in claim 1, wherein the at least one surface-modified disintegrant releases nitrogen or carbon dioxide or low molecular hydrocarbon.

8. The microcapsule as recited in claim 1, wherein the sheath of the at least one surface-modified disintegrant comprises a polymer or a copolymer selected from polyethylene (PE), polyurethane (PU), polypropylene (PP), polyvinyl chloride (PVC), polymethyl methacrylate (PMMA), polyvinylidene dichloride (PVDC), polyvinylidene dichloride-acrylonitrile copolymer, polyacrylonitrile (PAN), and poly(meth)acrylate.

9. The microcapsule as recited in claim 1, wherein the sheath of the at least one surface-modified disintegrant consists of polymethyl methacrylate, and the core of the at least one surface-modified disintegrant consists of a low molecular hydrocarbon.

10. The microcapsule as recited in claim 1, wherein the at least one surface-modified disintegrant has a zeta potential in the range from −0.9 to 0.8 mV.

11. The microcapsule as recited in claim 1, wherein a surface of the at least one surface-modified disintegrant is hydrophobized with a siloxane compound, a unipolar polyethylene, a unipolar hard polyethylene wax, or a raw sugar cane wax.

12. The microcapsule as recited in claim 1, wherein the core further comprises an inert material.

13. The microcapsule as recited in claim 12, wherein the inert material is selected from the group consisting of isopropylmyristate (IPM), a wax, polyethylene glycol (PEG), and a gasoline fraction with a carbon chain of more than 10 C-atoms.

14. The microcapsule as recited in claim 13, wherein the core further comprises a perfume oil.

15. A method of using the microcapsule as recited in claim 14 to release the perfume oil in the washing, drying or ironing of clothes, to release the perfume oil in the hair, or to release the perfume oil in the skin, the method comprising:
providing the microcapsule as recited in claim 14; and
allowing the microcapsule to release the perfume oil at a temperature of below 150° C. during the washing, drying or ironing of clothes, or during the care of hair or skin.

* * * * *